(12) United States Patent
Inoue

(10) Patent No.: US 10,413,155 B2
(45) Date of Patent: Sep. 17, 2019

(54) ENDOSCOPE SYSTEM AND THE METHOD OF CONTROLLING THE ENDOSCOPE

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

(\*) Notice: Subject to any disclaimer, the term of this patent is extended or adjusted under 35 U.S.C. 154(b) by 216 days.

(21) Appl. No.: 15/238,913

(22) Filed: Aug. 17, 2016

(65) Prior Publication Data

US 2016/0353970 A1 Dec. 8, 2016

Related U.S. Application Data

(63) Continuation of application No. PCT/JP2015/052799, filed on Feb. 2, 2015.

(30) Foreign Application Priority Data

Feb. 20, 2014 (JP) .................................. 2014-030256

(51) Int. Cl.
*A61B 1/00* (2006.01)
*G02B 23/24* (2006.01)
(Continued)

(52) U.S. Cl.
CPC ...... *A61B 1/00006* (2013.01); *A61B 1/00009* (2013.01); *A61B 1/0016* (2013.01);
(Continued)

(58) Field of Classification Search
CPC ..... A61B 1/041; A61B 1/0009; A61B 1/0006; A61B 1/158
(Continued)

(56) References Cited

U.S. PATENT DOCUMENTS

2003/0114742 A1\* 6/2003 Lewkowicz ....... A61B 1/00147
600/407
2007/0265502 A1\* 11/2007 Minosawa ......... A61B 1/00177
600/173
(Continued)

FOREIGN PATENT DOCUMENTS

CN 101543393 A 9/2009
EP 2 092 874 A1 8/2009
(Continued)

OTHER PUBLICATIONS

Extended Supplementary European Search Report dated Oct. 13, 2017 in European Patent Application No. 15 75 1956.2.
(Continued)

*Primary Examiner* — Patricia I Young
(74) *Attorney, Agent, or Firm* — Scully, Scott, Murphy & Presser, P.C.

(57) ABSTRACT

An endoscope system computes a distal end position of the endoscope or a position of the desired imaging target. An image taken of the desired imaging target is recorded. A position of the desired imaging target is computed and recorded. A current image taken by the imaging unit is compared with the image of the desired imaging target already recorded. A first driving amount for driving the field-of-view adjustment mechanism is computed such that the desired imaging target is positioned on an axis of sighting of the imaging unit. A second driving amount for driving the field-of-view adjustment mechanism is computed in such a way as to include a center of the image of the desired imaging target. The field-of-view adjustment mechanism is driven from either one of the first driving amount or the second driving amount.

12 Claims, 20 Drawing Sheets

(51) Int. Cl.
| | |
|---|---|
| *A61B 5/06* | (2006.01) |
| *A61B 1/045* | (2006.01) |
| *A61B 1/313* | (2006.01) |
| *A61B 17/00* | (2006.01) |
| *G06K 9/52* | (2006.01) |
| *G06K 9/62* | (2006.01) |
| *G06T 7/00* | (2017.01) |
| *G06T 7/60* | (2017.01) |
| *H04N 5/232* | (2006.01) |
| *G06T 7/70* | (2017.01) |

(52) U.S. Cl.
CPC ...... *A61B 1/00045* (2013.01); *A61B 1/00149* (2013.01); *A61B 1/00154* (2013.01); *A61B 1/00172* (2013.01); *A61B 1/00183* (2013.01); *A61B 1/045* (2013.01); *A61B 1/3132* (2013.01); *A61B 5/065* (2013.01); *A61B 17/00234* (2013.01); *G02B 23/2476* (2013.01); *G02B 23/2484* (2013.01); *G06K 9/52* (2013.01); *G06K 9/6215* (2013.01); *G06T 7/0012* (2013.01); *G06T 7/60* (2013.01); *G06T 7/70* (2017.01); *H04N 5/23296* (2013.01); *A61B 1/0002* (2013.01); *G06T 2207/30004* (2013.01)

(58) Field of Classification Search
USPC .......................................................... 348/65
See application file for complete search history.

(56) References Cited

U.S. PATENT DOCUMENTS

| | | | |
|---|---|---|---|
| 2009/0148017 A1* | 6/2009 | Inoue | A61B 1/04 382/128 |
| 2009/0203964 A1* | 8/2009 | Shimizu | A61B 1/041 600/109 |
| 2010/0076263 A1 | 3/2010 | Tanaka et al. | |
| 2010/0277650 A1* | 11/2010 | Matsuzaki | A61B 1/00009 348/700 |
| 2014/0323801 A1 | 10/2014 | Konno et al. | |

FOREIGN PATENT DOCUMENTS

| | | |
|---|---|---|
| EP | 2 158 834 A1 | 3/2010 |
| JP | H09-26547 A | 1/1997 |
| JP | H10-295639 A | 11/1998 |
| JP | 2007-151862 A | 6/2007 |
| JP | 2007-301378 A | 11/2007 |
| JP | 4382894 B2 | 12/2009 |
| JP | 2011-234871 A | 11/2011 |
| JP | 2013-192773 A | 9/2013 |
| WO | 2013/054944 A1 | 4/2013 |
| WO | 2013/067025 A1 | 5/2013 |

OTHER PUBLICATIONS

International Search Report dated Apr. 21, 2015 issued in PCT/JP2015/052799.

* cited by examiner

ENDOSCOPE SYSTEM AND THE METHOD OF CONTROLLING THE ENDOSCOPE

CROSS-REFERENCE TO RELATED APPLICATIONS

This application is a continuation claiming priority on the basis of Japan Patent Application No. 2014-030256 applied in Japan on Feb. 20, 2014 and based on PCT/JP2015/052799 filed on Feb. 2, 2015. The contents of both the PCT application and the Japan Application are incorporated herein by reference.

BACKGROUND OF THE INVENTION AND RELATED ART STATEMENT

The present invention relates to an endoscope system that is inserted through the body cavity of a patient for surgical operation to view, and apply treatments or the like to, the interior of the patient's body cavity.

In laparoscopic operation, there are multiple incisions cut open in the abdomen or the like of a patient through which various medical instruments such as cameras, forceps and (electric) scalpel are inserted for viewing and treatments of an affected site while checking up with images taken by a camera. This laparoscopic operation is less invasive of the patient because of limited incision area.

Japanese Patent Publication JP(A) 2007-301378 discloses the technology of driving an electrically-operated joint of an endoscope such that the tilt angle of a trocar adapted to guide various medical instruments inserted through the patient's abdomen is detected to allow the area of interest to come in the field of view of the endoscope.

Japanese Patent No. 4382894 discloses the technology of driving an endoscope such that feature points on a treatment tool are extracted by image processing to allow the treatment tool to come in the field of view.

SUMMARY OF INVENTION

According to one embodiment, an endoscope system includes an endoscope including an imaging unit that is capable of taking an image of an imaging target, a field-of-view adjustment mechanism for varying an orientation of the imaging unit and a driver unit for driving the field-of-view adjustment mechanism, an endoscopic position sensor for detecting a position of the endoscope in the body cavity, a distance measurement unit for measuring a distance from a distal end of the endoscope to the imaging target, a position computation unit for computing positions of the distal end of the endoscope and the imaging target on the basis of information from the endoscopic position sensor and the distance measurement unit, a position storage unit for storing a position of the imaging target computed by the position computation unit, a first driving-amount computation unit for computing a driving amount for the field-of-view adjustment mechanism using the position stored in the position storage unit and the position of the distal end of the endoscope, an image storage unit for storing the image of the imaging target taken by the imaging unit, a comparison unit for comparing the image of the imaging target stored in the image storage unit with a newly taken image of the imaging target, a second driving-amount computation unit for computing a driving amount for the field-of-view adjustment mechanism depending on a result of comparison by the comparison unit, and a determination unit for determining which is used, a first driving amount computed by the first driving-amount computation unit or a second driving amount computed by the second driving-amount computation unit, to drive the driver unit.

According to one embodiment, there is an endoscope control process provided for controlling an endoscope including an imaging unit and a field-of-view adjustment mechanism for varying an orientation of the imaging unit in which the field-of-view adjustment mechanism is controlled while capturing a desired imaging target, the endoscope control process includes a position computation step of computing a distal end position of the endoscope or a position of the desired imaging target, an image recording step of recording an image taken of the desired imaging target, a position storage step of computing and recording a position of the desired imaging target, an image comparison step of comparing a current image taken by the imaging unit with the image of the desired imaging target already recorded, a first driving-amount computation step of computing a driving amount for driving the field-of-view adjustment mechanism such that the desired imaging target is positioned on an axis of sighting of the imaging unit, a second driving-amount computation step of computing a driving amount for driving the field-of-view adjustment mechanism in such a way as to include a center of the image of the desired imaging target, and a driving step of driving the field-of-view adjustment mechanism from the driving amount computed in either one of the first driving-amount computation step or the second driving-amount computation step.

DESCRIPTION OF EMBODIMENTS

Some embodiments will now be explained.

Figure 1:
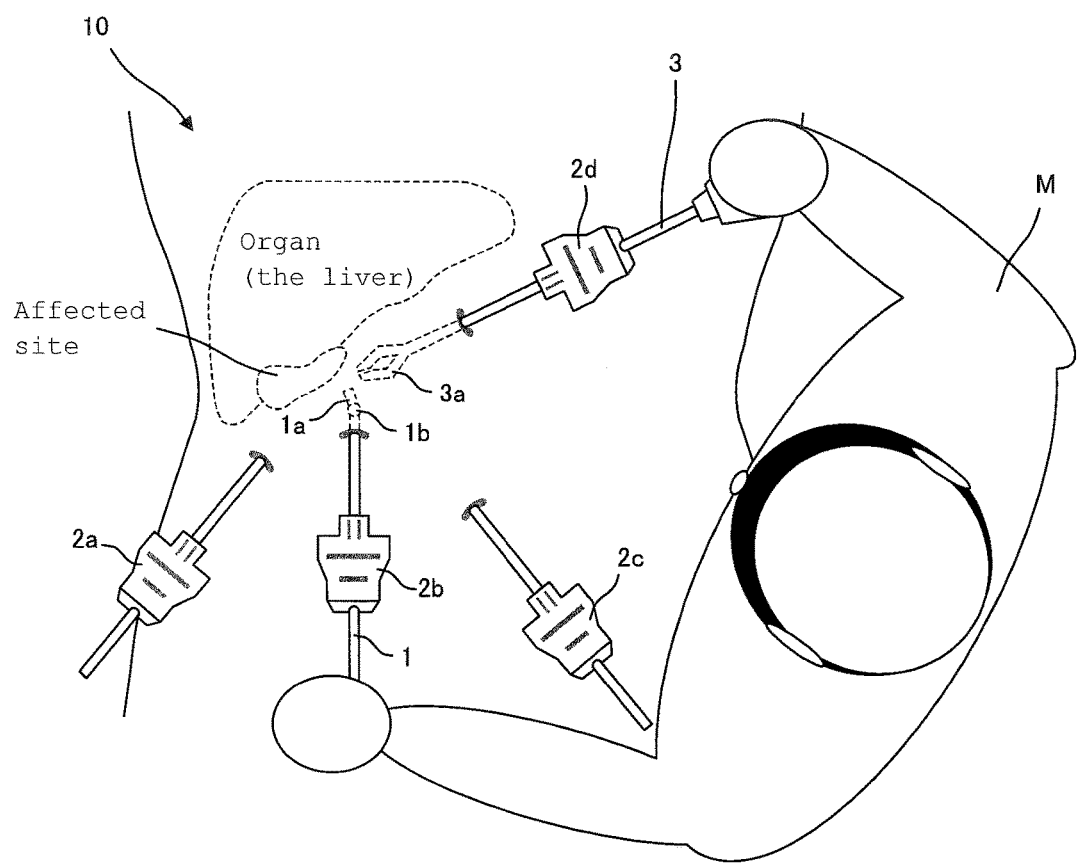
FIG. 1 is a schematic view of one example of the endoscope system according to one embodiment.

FIG. 1 is illustrative in schematic of one example of the endoscope system 10 according to the embodiment described herein.

In laparoscopic surgery, tubes called trocars (channels) 2a to 2d are inserted through incisions cut open in the body wall of a patient, and various medical instruments are inserted into the patient's body cavity by way of these trocars 2a to 2d. FIG. 1 shows that the endoscope 1 is being inserted through the trocar 2b and a treatment tool 3 such as forceps is being inserted through the trocar 2d. The distal end of the endoscope 1 inserted through the patient's body cavity by way of the trocar 2b is provided with an imaging unit 1a and a field (of view) adjustment mechanism 1b capable of adjusting angles or the like such that an affected site, a treatment tool or the like comes within the field of view. A distal-end portion of the treatment tool 3 inserted into the patient's body cavity by way of the trocar 2d is provided with a distal-end portion 3a such as a grip. A surgeon M adjusts the field-of-view adjustment mechanism 1b of the endoscope 1 and operates the treatment tool 3 while viewing a display unit 6 such as a monitor on which an image of the affected site taken by the imaging unit 1a appears, thereby opening or closing the distal-end portion 3a for treatment of the affected site.

Figure 2:
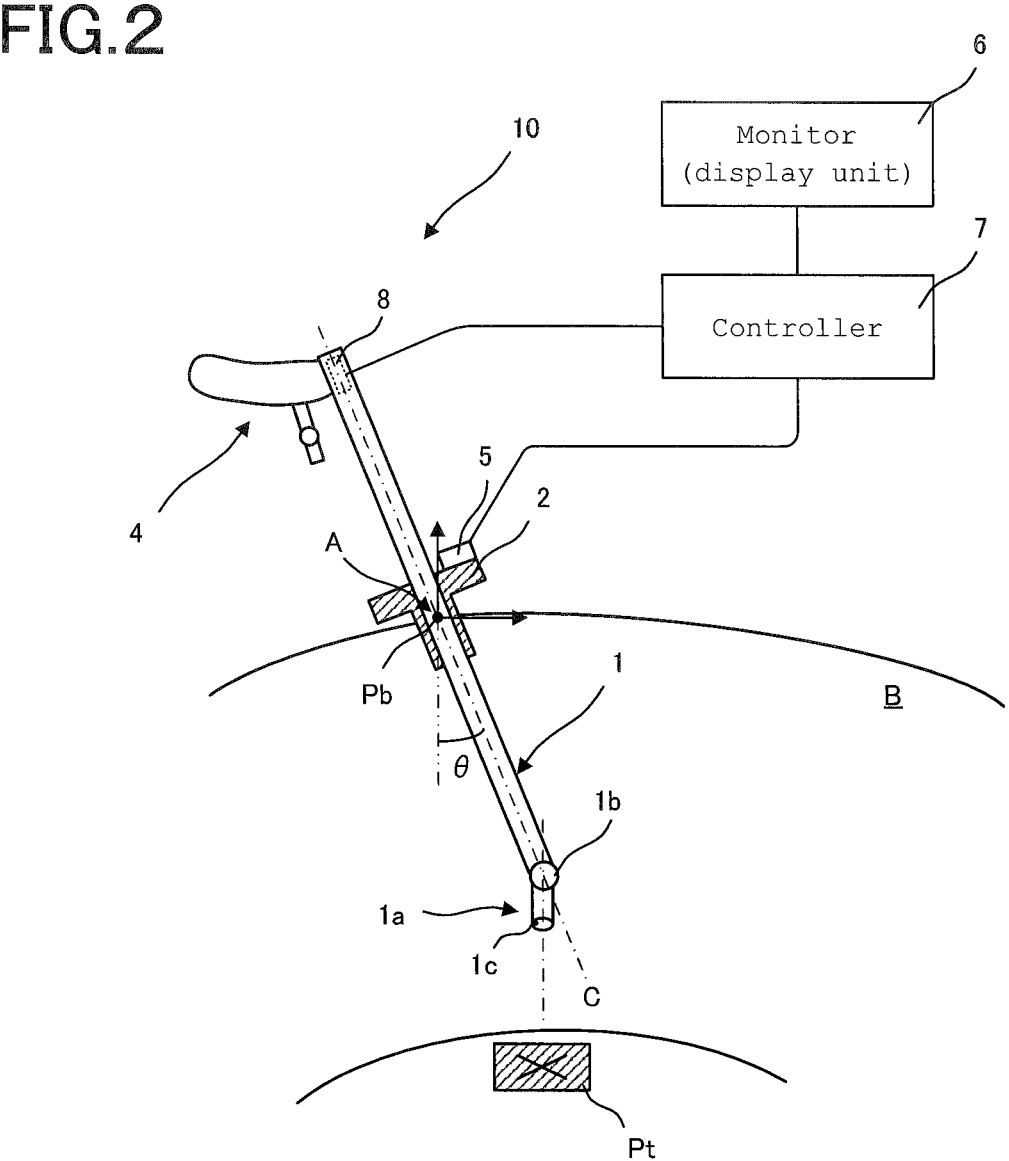
FIG. 2 is a schematic view of one example of the endoscope system according to the first embodiment.
Figure 3:
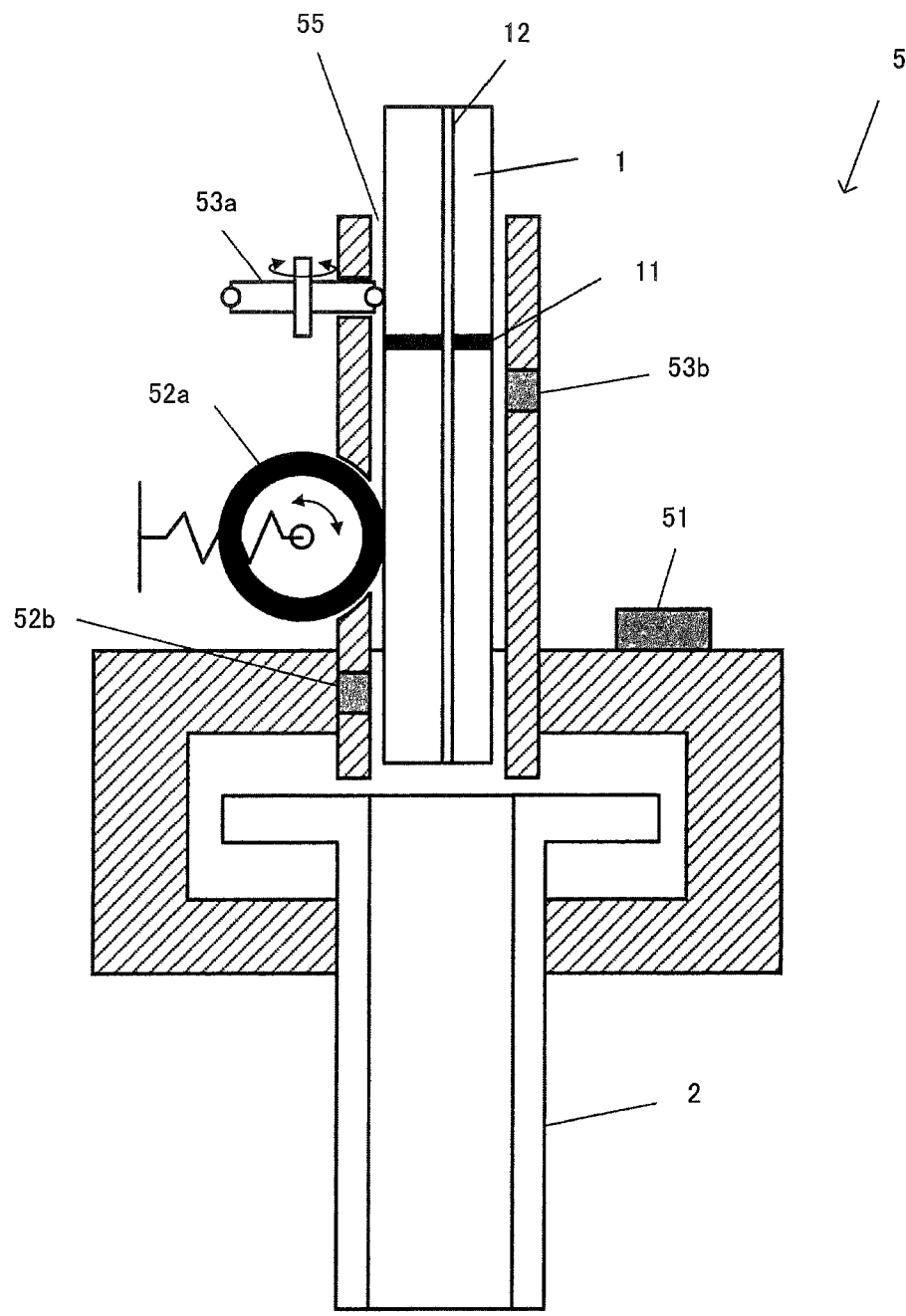
FIG. 3 is a schematic view of the trocar sensor in the endoscope system according to the first embodiment.

FIG. 2 is illustrative in schematic of one example of the endoscope system 10 according to the first embodiment, and FIG. 3 is illustrative in schematic of the trocar sensor 5 in the endoscope system 10 according to the second embodiment.

The endoscope 1 is inserted into the body cavity B through the trocar 2. In the endoscope 1, the field-of-view adjustment mechanism 1b is adjusted by operation of the operating input unit 4 to direct the imaging unit 1a to an imaging target Pt. Preferably, the distal end of the imaging unit 1a is provided with a distance sensor 1c that works as a position sensor adapted to measure a distance to the imaging target Pt.

It is here to be noted that the field-of-view adjustment mechanism 1b includes at least one electrically operated rotatable joint. More preferably, the electrically operated joint includes a succession of joints because the directionality of the imaging unit 1a is more enhanced. Alternatively, the field-of-view adjustment mechanism 1b may be located outside the body cavity.

The trocar 2 according to the embodiment described herein includes a trocar sensor 5, as depicted in FIG. 3. The trocar sensor 5 includes, and is constructed of, a tilt angle detection sensor 51, an amount-of-advanceable/retractable-movement detection sensor 52 and an amount-of-rotation detection sensor 53.

The tilt angle detection sensor 51 is provided to detect in which direction the trocar 2 turns with respect to a reference coordinate system. The reference coordinate system here is the one that is defined relative to a fixed object such as a patient or the ground; for instance, there is the mention of a coordinate system A with the fulcrum Pb of FIG. 2 as center. A variety of sensors such as an acceleration sensor may be used as the tilt angle detection sensor 51. The acceleration sensor may detect an acceleration applied thereon to detect in which direction the trocar 2 turns, that is, the tilt angle θ of the trocar 2 with respect to such a coordinate system as shown in FIG. 2.

The amount-of-advanceable/retractable-movement detection sensor 52 is provided for detection of the amount of advanceable and retractable movement of a medical instrument such as the endoscope 1 inserted through the trocar 2 in its insertion direction. A surgeon such as a physician inserts or ejects a medical instrument through the trocar 2 to operate and move the medical instrument within the patient's body to an unerring position. With the amount-of-advanceable/retractable-movement detection sensor 52, it is possible to detect the insertion position of the medical instrument relative to the trocar 1 in the form of the amount of advanceable and retractable movement. FIG. 2 shows the center axis C of the trocar 1 in the insertion direction by a dashed line. The amount-of-advanceable/retractable-movement detection sensor 52 detects the amount of movement parallel with that center axis C in the form of the amount of advanceable and retractable movement. In the embodiment described herein, the amount-of-advanceable/retractable-movement detection sensor 52 is made up of a combined amount-of-advanceable/retractable-movement detection roller 52a and photosensor 52b. Preferably in this case, the medical instrument such as the endoscope 1 is provided with a advanceable/retractable position detection mark 11 that is capable of being detected by the photosensor 52b.

The amount-of-rotation detection sensor 53 is provided for detection of the amount of rotation of a medical instrument that rotates in association with operation as by a surgeon. By rotational operation about the center axis C of a medical instrument inserted through the insertion hole 55, it is possible to change the direction of an end effector mounted at the distal end of the medical instrument within the patient's body. The amount-of-rotation detection sensor 53 detects this amount of rotation so that in which direction the end effector of the medical instrument turns can be detected. The amount-of-rotation detection sensor 53 here is made up of a combined amount-of-rotation detection roller 53a and photosensor 53b. Preferably in this case, the medical instrument such as the endoscope 1 is provided with a advanceable/retractable position detection mark 12 that is capable of being detected by the photosensor 53b.

While the trocar sensor 5 located in the trocar 2 has been explained, it is to be understood that sensors having various forms may be used instead. For instance, a mechanical sensor using a roller is here used for the purpose of detecting the amount of advanceable/retractable movement and rotation, but the amount of advanceable/retractable movement and rotation may also be detected by means of an optical sensor capable of detecting the amount and direction of movement of a surface used for a laser mouse. In this case, the amounts of advanceable/retractable movement and rotation may be detected by means of a single optical sensor. For medical system according to the embodiment described herein, it is required to know the direction or the direction and position of a medical instrument inserted through the body of a patient. In the embodiment described herein, these are easy to detect because various sensors are located within the trocar 2; however, an external sensor located outside the trocar 2 may be used to detect the direction or the direction and position of the medical instrument. For instance, the tilt angle detection sensor 51 located in the trocar 2 may be located directly on the medical instrument side.

Figure 4:
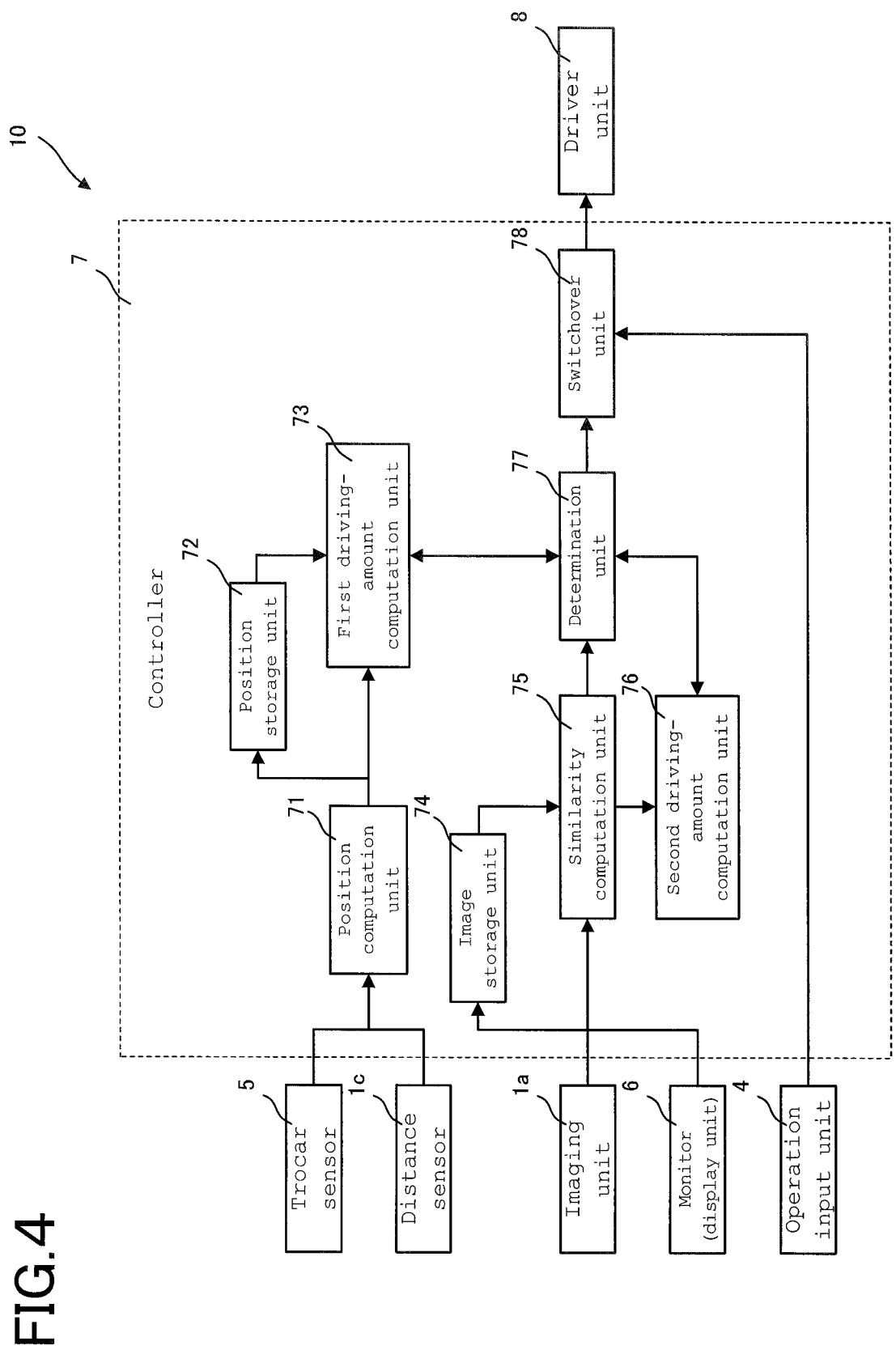
FIG. 4 is illustrative of one example of the control system for the endoscope system according to the first embodiment.

FIG. 4 is illustrative of one example of the control system for the endoscope system 10 according to the first embodiment.

The endoscope system 10 is controlled by a control unit (controller) 7. A position computation unit 71 is adapted to compute the position of the imaging target Pt shown in FIG. 2 on the basis of information entered from the trocar sensor 5 and distance sensor 1c. A position storage unit 72 is adapted to store the position of the imaging target Pt computed by the position computation unit 71. A first driving-amount computation unit 73 is adapted to compute the driving amount for a driver unit 8 that drives the field-of-view adjustment mechanism 1b shown in FIG. 2 such that the position of the imaging target Pt computed by the position computation unit 71 lies on the axis of sighting of the endoscope. The driver unit 8 may take a form of directly rotating the joint by an electric motor or the like, or a form of rotating the joint indirectly by way of a wire or the like.

The image storage unit 74 is adapted to store an image taken by the imaging unit 1a. The images to be stored may be at least a part of the images taken by the imaging unit 1a. A similarity computation unit 75 working as a comparison unit is adapted to compare the previous (before movement) images taken by the imaging unit 1a and stored in the image storage unit 74 with current (after movement) images taken by the imaging unit 1a to compute the degree of similarity. The degree of similarity may be computed by a method such as a conventional template matching method. A second driving-amount computation unit 76 is adapted to compute the driving amount for the driver unit 8 that drives the field-of-view adjustment mechanism 1b shown in FIG. 2 such that the imaging unit 1a directs from the position where the imaging unit 1a takes the current images to the position where the previously stored images were taken.

A determination unit 77 is adapted to determine which is used, a sensor-based first driving amount computed by the first driving-amount computation unit 73 or an image-based second driving amount computed by the second driving-amount computation unit 76, from the degree of similarity computed by the similarity computation unit 75.

A switchover unit 78 is adapted to switch between a normal mode and a tracking mode in response to a signal entered from the operation input unit 4. In the normal mode, as the imaging unit 1a moves, it causes the field of view to move too, and in the tracking mode, the imaging target Pt remains fixed in the field of view even when the imaging unit 1a moves.

It is here to be appreciated that there may be a display unit 6 provided for displaying at least one of the result of determination of the determination unit 77, the mode state switched by the switchover unit 78 and the image.

Figure 5:
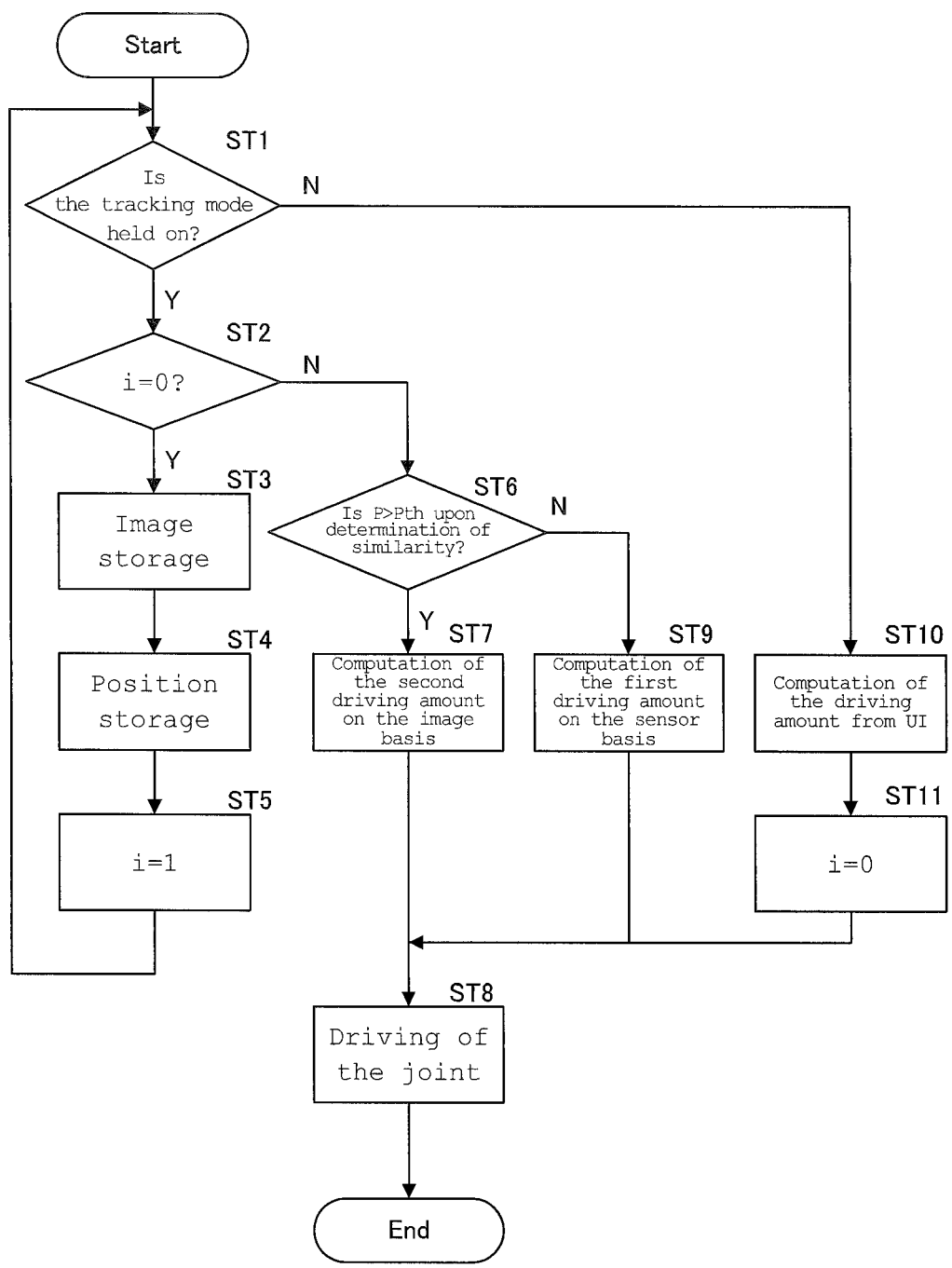
FIG. 5 is illustrative of one example of the control flowchart for the endoscope according to the first embodiment.

FIG. 5 is illustrative of one example of the control flowchart for the endoscope system 10 according to the first embodiment.

In the endoscope system 10 according to the first embodiment, it is first determined in Step 1 whether or not the tracking mode of the switchover unit 78 is held on (ST1).

When the tracking mode of the switchover unit 78 is held on in Step 1, the processing goes to Step 2 in which it is determined whether or not the counter is i=0 (ST2).

When the counter is i=0 in Step 2, the processing goes to Step 3 in which the image storage unit 74 stores a reference image $Pt_0$ of the imaging target Pt that is currently being taken by the imaging unit 1a (ST3).

Figure 6A:
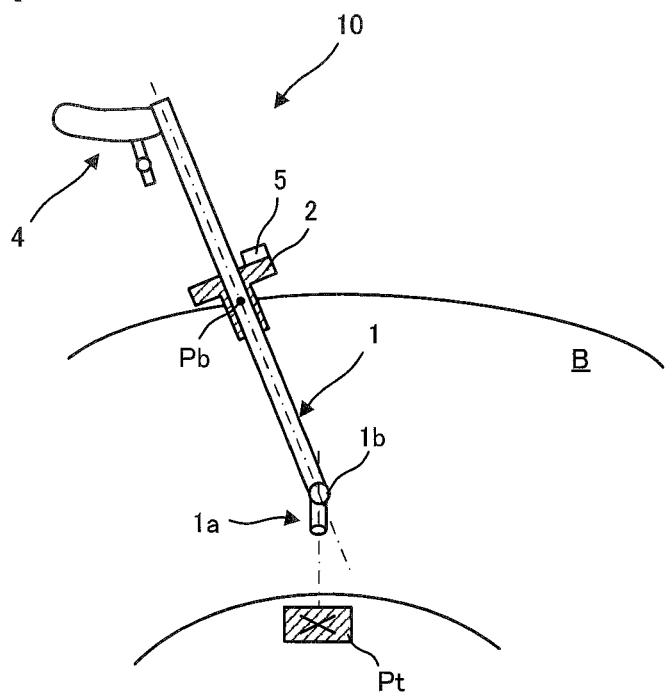
FIGS. 6A, 6B and 6C are illustrative of a state in which the endoscope according to the first embodiment stores an image.
Figure 6B:
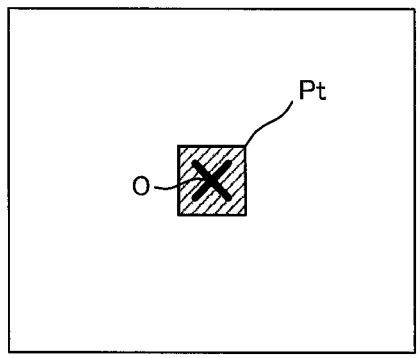
Figure 6C:
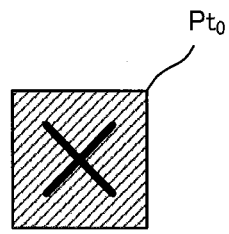

FIGS. 6A, 6B and 6C are illustrative of a state in which images are stored by the endoscope system 10 according to the first embodiment: FIG. 6A is illustrative of the endoscope 1 according to the first embodiment, which directs to the imaging target Pt, FIG. 6B is illustrative of the then display unit 6, and FIG. 6C is illustrative of the reference image $Pt_0$.

In order for the imaging target Pt to appear on the display unit as shown in FIG. 6B, the imaging unit 1a of the endoscope 1 is operated by the surgeon as shown in FIG. 6A. In this state, as the image storage unit 74 is instructed by the surgeon to store the images of the imaging target Pt, it allows the reference image $Pt_0$ of the imaging target Pt to be stored as shown in FIG. 6C.

Then, the processing goes to Step 4 in which the positions of the distal end of the endoscope and the imaging target Pt are computed by the position computation unit 71 on the basis of information entered from the trocar sensor 5 and distance sensor 1c and stored by the position storage unit 72 (ST4).

Then, the processing goes to Step 5 in which the counter is set to i=1 (ST5), and returns back to Step 1.

In Step 2, when the counter is not i=0, the processing goes to Step 6 in which the degree of similarity between the reference image $Pt_0$ of the previously stored imaging target Pt and the current reference image $Pt_1$ of the imaging target Pt is computed by the similarity computation unit 75 and whether or not the degree of similarity P is greater than a given value Pth is determined by the determination unit 77 (ST6). In other words, which is used, the sensor-based first driving amount computed by the first driving-amount computation unit 73 or the image-based second driving amount computed by the second driving-amount computation unit 76, is determined by the determination unit 77.

In Step 6, when the degree of similarity P is greater than the given value Pth, the processing goes to Step 7 in which the image-based second driving amount computed by the second driving-amount computation unit 76 is computed (ST7). Then, the processing goes to Step 8 in which the joint is driven according to the second driving amount (ST8).

Figure 7A:
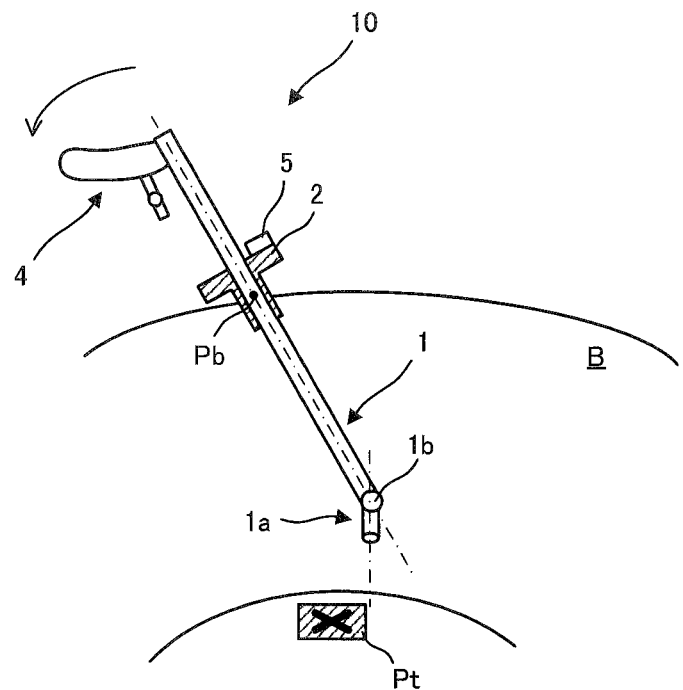
FIGS. 7A, 7B and 7C are illustrative of the endoscope after moving to a first position of the endoscope system according to the first embodiment.
Figure 7B:
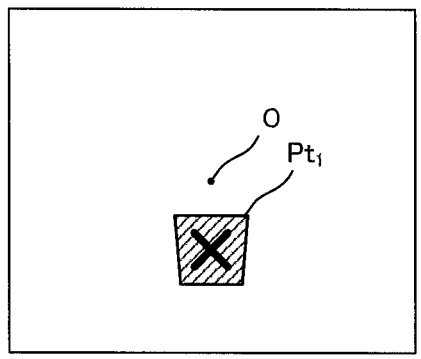
Figure 7C:
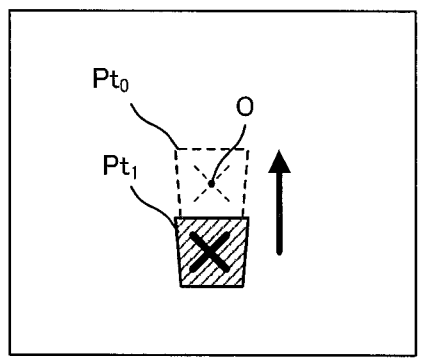

FIGS. 7A, 7B and 7C are illustrative of the endoscope 1 after moving to the first position of the endoscope system 10 according to the first embodiment and the then display unit 6: FIG. 7A is illustrative of the endoscope 1 after moving to the first position of the endoscope system 10 according to the first embodiment, FIG. 7B is illustrative of the then display unit 6, and FIG. 7C is illustrative of a target position for the image $Pt_1$ of the imaging target Pt.

Figure 8A:
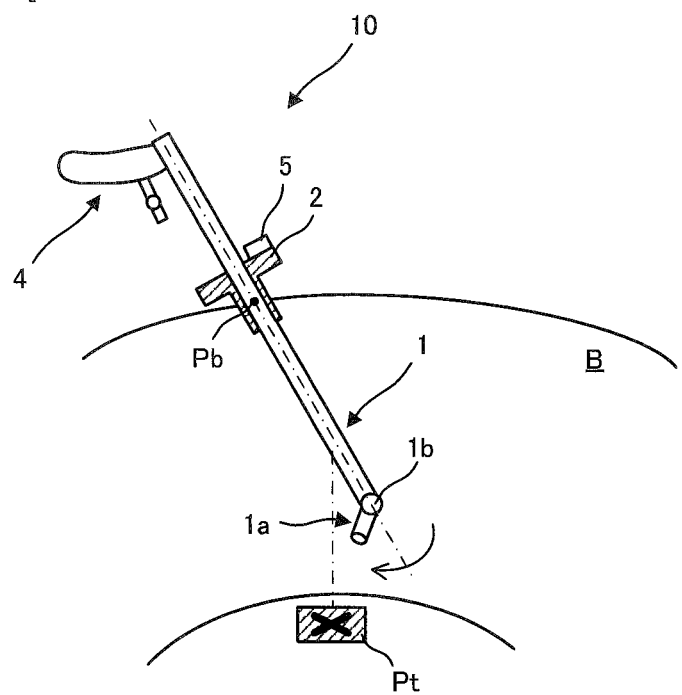
FIGS. 8A and 8B are illustrative of a state in which the joint is driven by the endoscope 1 in the endoscope system according to the first embodiment.
Figure 8B:
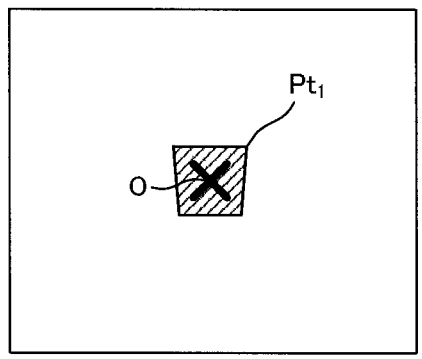

FIGS. 8A and 8B are illustrative of the joint that is driven by the endoscope 1 in the endoscope system 10 according to the first embodiment: FIG. 8A is illustrative of the joint that is being driven by the endoscope 1 of the endoscope system 10 according to the first embodiment, and FIG. 8B is illustrative of the then display unit 6.

As the endoscope 1 is moved by the surgeon from the storage position shown in FIG. 6A to the first position shown in FIG. 7A, the reference image $Pt_0$ of the imaging target Pt stored as shown in FIG. 6B looks like the current image $Pt_1$ of the imaging target Pt, as shown in FIG. 7B. The reference image $Pt_0$ of the imaging target Pt stored in the image storage unit 74 and the current image $Pt_1$ of the imaging target Pt are here compared by the similarity computation unit 75 in the control unit 7 for similarity computation.

When the degree of similarity P is greater than the predetermined value Pth, the direction and amount of movement in which the current image $Pt_1$ of the imaging target Pt is moved in such a way as to include at least the center O of the field of view, just like the reference image $Pt_0$ of the imaging target Pt stored in the image storage unit 74, are here computed by the second driving-amount computation unit 76, as shown in FIG. 7C. That is, the second driving amount for driving the field-of-view adjustment mechanism 1b is computed by the second driving-amount computation unit 76.

After that, the field-of-view adjustment mechanism 1b is driven, as shown in FIG. 8A, to vary the orientation of the imaging unit 1a such that the current image $Pt_1$ of the imaging target Pt is nearly centered in such a way as to include at least the center O of the field of view, as shown in FIG. 8B.

In Step 6, when the degree of similarity P is less than the predetermined value Pth, the processing goes to Step 9 in which the sensor-based first driving amount computed by the first driving-amount computation unit 73 is computed (ST9). Then, the joint is driven according to the first driving amount in Step 8.

Figure 9A:
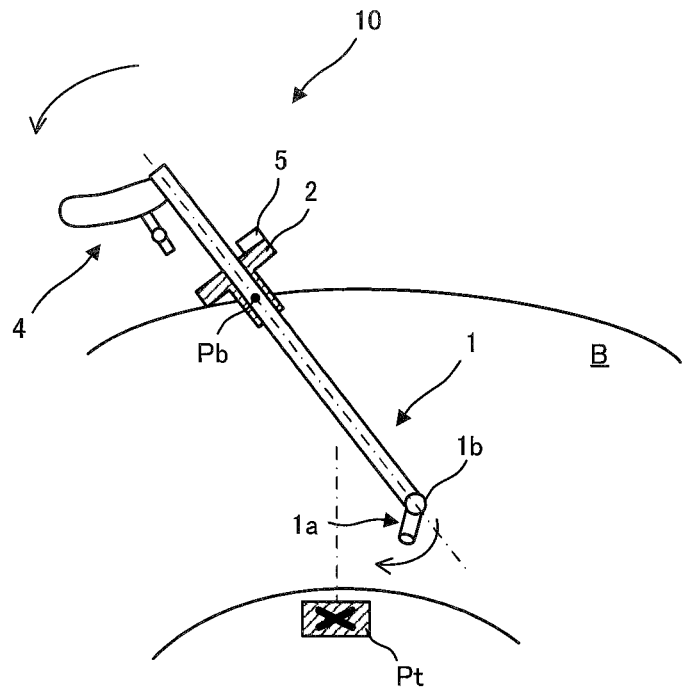
FIGS. 9A, 9B and 9C are illustrative of the endoscope after moving to a second position of the endoscope system according to the first embodiment.
Figure 9B:
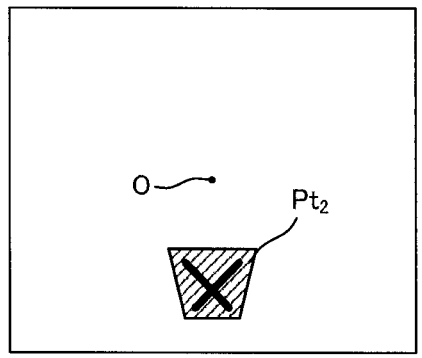
Figure 9C:
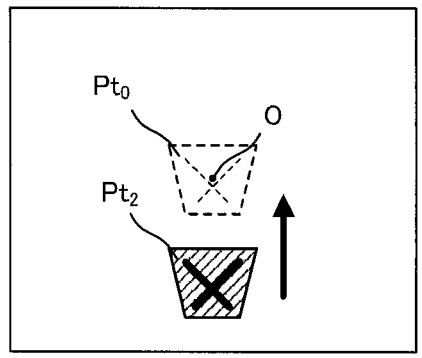

FIGS. 9A, 9B and 9C are illustrative of the endoscope 1 after moving to the second position of the endoscope system 10 according to the first embodiment and the then display unit 6: FIG. 9A is illustrative of the endoscope 1 after moving to the second position of the endoscope system 10 according to the first embodiment, FIG. 9B is illustrative of the then display unit 6, and FIG. 9C is illustrative of a target position for an image $Pt_2$ of the imaging target Pt.

Figure 10A:
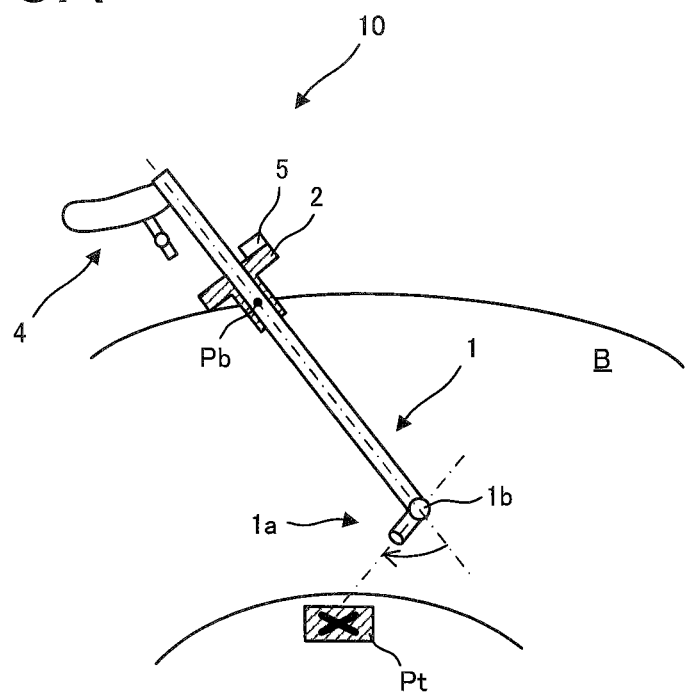
FIGS. 10A and 10B are illustrative of a state in which the joint is driven by the endoscope system according to the first embodiment.
Figure 10B:
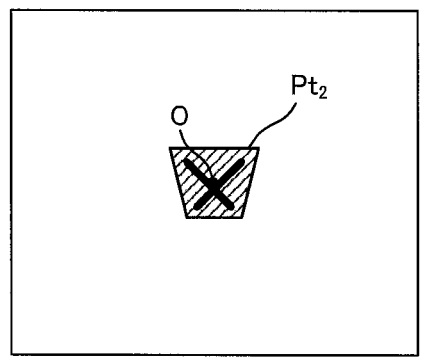

FIGS. 10A and 10B are illustrative of the joint that is driven by the endoscope system 10 according to the first embodiment and the then display unit 6: FIG. 10A is illustrative of the joint that is being driven by the endoscope system 10 according to the first embodiment, and FIG. 10B is illustrative of the then display unit 6.

As the endoscope 1 is moved by the surgeon from the storage position shown in FIG. 6A to the second position shown in FIG. 9A, the reference image $Pt_0$ of the imaging target Pt stored as shown in FIG. 6B looks like the current image $Pt_2$ of the imaging target Pt, as shown in FIG. 9B. The reference image $Pt_0$ of the imaging target Pt stored in the image storage unit 74 and the current image $Pt_2$ of the imaging target Pt are compared by the similarity computation unit 75 in the control unit 7 for similarity computation.

When the degree of similarity P is less than the predetermined value Pth, the direction and angle of the field-of-view adjustment mechanism 1b for nearly centering the current image $Pt_2$ of the imaging target Pt in such a way as to include at least the center O of the field of view, just like the reference image $Pt_0$ of the imaging target Pt stored in the image storage unit 74, are here computed by the similarity computation unit 75 in the control unit 7 from measurements obtained through the trocar sensor 5 and distance sensor 1c. In other words, the second driving amount for driving the field-of-view adjustment mechanism 1b is computed by the second driving-amount computation unit 76.

After that, the field-of-view adjustment mechanism 1b is driven, as shown in FIG. 10A, to vary the orientation of the imaging unit 1a such that the current image $Pt_2$ of the imaging target Pt is nearly centered in such a way as to include at least the center O of the field of view, as shown in FIG. 10B.

It is here to be appreciated that in Step 1, when the tracking mode of the switchover unit 78 is held off, the processing goes to Step 10 in which the driving amount is computed from a user interface (ST10). Then, the processing goes to Step 11 in which the counter is set to i=0 (ST11). After that, the joint is driven in Step 8 according to the first driving amount.

As described above, the endoscope system 10 according to one embodiment includes an endoscope 1 including an imaging unit 1a that is capable of taking an image of a imaging target Pt, a field-of-view adjustment mechanism 1b for varying an orientation of the imaging unit 1a, an operation input unit 4 for operating the field-of-view adjustment mechanism 1b and a driver unit for driving the field-of-view adjustment mechanism 1b, an endoscopic position sensor (trocar sensor) 5 for detecting a position of the endoscope 1 in the body cavity B, a distance measurement unit (distance sensor) 1c for measuring a distance from a distal end of the endoscope 1 to the imaging target Pt, a position computation unit 71 for computing positions of the distal end of the endoscope and the imaging target Pt on the basis of information from the endoscopic position sensor 5 and distance measurement unit 1c, a position storage unit 72 for storing a position computed by the position computation unit 71, a first driving-amount computation unit 73 for computing a driving amount for the field-of-view adjustment mechanism 1b depending on position information from the position storage unit 72, an image storage unit 74 for storing an image $Pt_0$ of the imaging target Pt taken by the imaging unit 1a, a comparison unit 75 for comparing the image $Pt_0$ of the imaging target Pt stored in the image storage unit 74 with a newly taken image $Pt_1$ of the imaging target Pt, a second driving-amount computation unit 76 for computing a driving amount for the field-of-view adjustment mechanism 1b depending on a result of comparison by the comparison unit 75, and a determination unit 77 for determining which is used, a first driving amount computed by the first driving-amount computation unit 73 or a second driving amount computed by the second driving-amount computation unit 76, to drive the driver unit 8. It is thus possible to control the endoscope 1 such that the area of interest Pt remains within the field of view even when there are changes in an environment in the body cavity B.

The comparison unit 75 includes the image $Pt_0$ of the imaging target Pt stored in the image storage unit 74, the newly taken image $Pt_1$ of the imaging target Pt and the similarity computation portion 75, and the determination unit 77 makes the determination depending on the degree of similarity computed by the similarity computation portion 75. It is thus possible to improve on precision.

Further, the present invention provides a process of controlling the endoscope 1 according to one embodiment, which endoscope 1 includes an imaging unit 1a and a field-of-view adjustment mechanism 1b for varying the orientation of the imaging unit 1a wherein the field-of-view adjustment mechanism 1b is controlled while capturing the desired imaging target, the process including a position computation step of computing the distal end position of the endoscope 1 or the position of the desired imaging target, an image recording step of recording an image taken of the desired imaging target, a position storage step of computing and recording the position of the desired imaging target, an image comparison step of comparing a current image taken by the imaging unit 1a with the previously recorded image of the desired imaging target, a first driving-amount computation step of computing a driving amount for driving the field-of-view adjustment mechanism 1b such that the desired imaging target is positioned on the axis of sighting of the imaging unit 1a, a second driving-amount computation step of computing a driving amount for driving the field-of-view adjustment mechanism 1a in such a way as to include the center of the image of the desired imaging target, and a driving step of driving the field-of-view adjustment mechanism 1b from the driving amount computed in either one of the first and second driving-amount computation steps. It is thus possible to control the endoscope 1 such that the area of interest Pt remains within the field of view, even when there are changes in environments within the body cavity B.

In the first driving-amount computation step in the endoscope control process, when both the images compared in the image comparison step are determined as having a low degree of similarity, the driving amount is computed, and in the second driving-amount computation step, when both the images compared in the image comparison step are determined as having a high degree of similarity, the driving amount is computed. It is thus possible to improve on precision.

Reference is then made to a certain case where the degree of similarity is determined as being low for the reason of the presence of an obstacle.

Figure 11A:
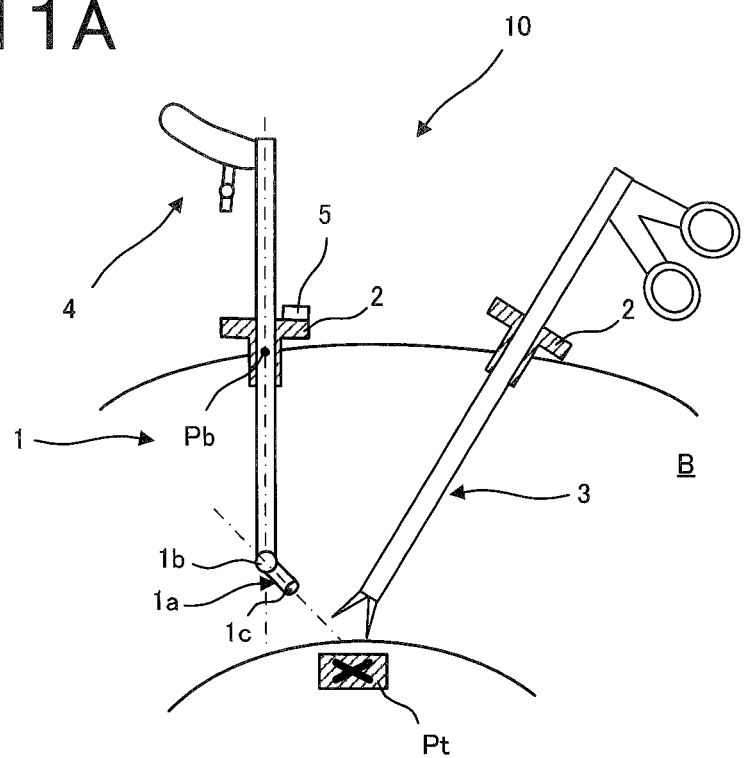
FIGS. 11A and 11B are illustrative of the endoscope system according to the first embodiment wherein there is an obstacle.
Figure 11B:
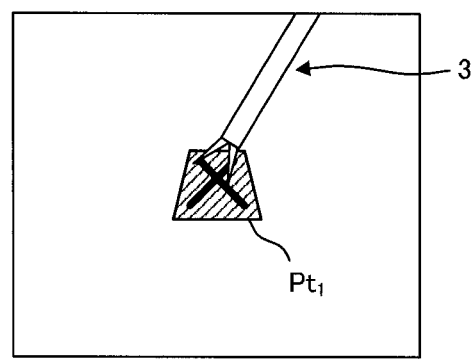

FIGS. 11A and 11B are shows that there is an obstacle in the endoscope system 10 according to the first embodiment and the then display unit 6: FIG. 11A shows that there is an obstacle in the endoscope system 10 according to the first embodiment, and FIG. 11B is illustrative of the then display unit 6.

When a treatment tool 3 such as forceps is used by the surgeon together with the endoscope 1, there is sometimes an obstacle 3 such as forceps present in front of the imaging target Pt, as depicted in FIG. 11A. The reference image $Pt_0$ of the imaging target Pt stored in the image storage unit 74 is compared by the similarity computation unit 75 in the control unit 7 with the current image $Pt_1$ of the imaging target Pt for similarity computation.

When the degree of similarity P is less than the given value Pth, the direction and angle of the field-of-view adjustment mechanism 1b for centering the current image $Pt_1$ of the imaging target Pt are here computed by the first driving-amount computation unit 73 from measurements obtained from the trocar sensor 5 and distance sensor 1c, as shown in FIG. 11B. In other words, the first driving amount for driving the field-of-view adjustment mechanism 1b is computed by the first driving-amount computation unit 73, and the field-of-view adjustment mechanism 1b is driven according to the thus computed first driving amount.

Figure 12:
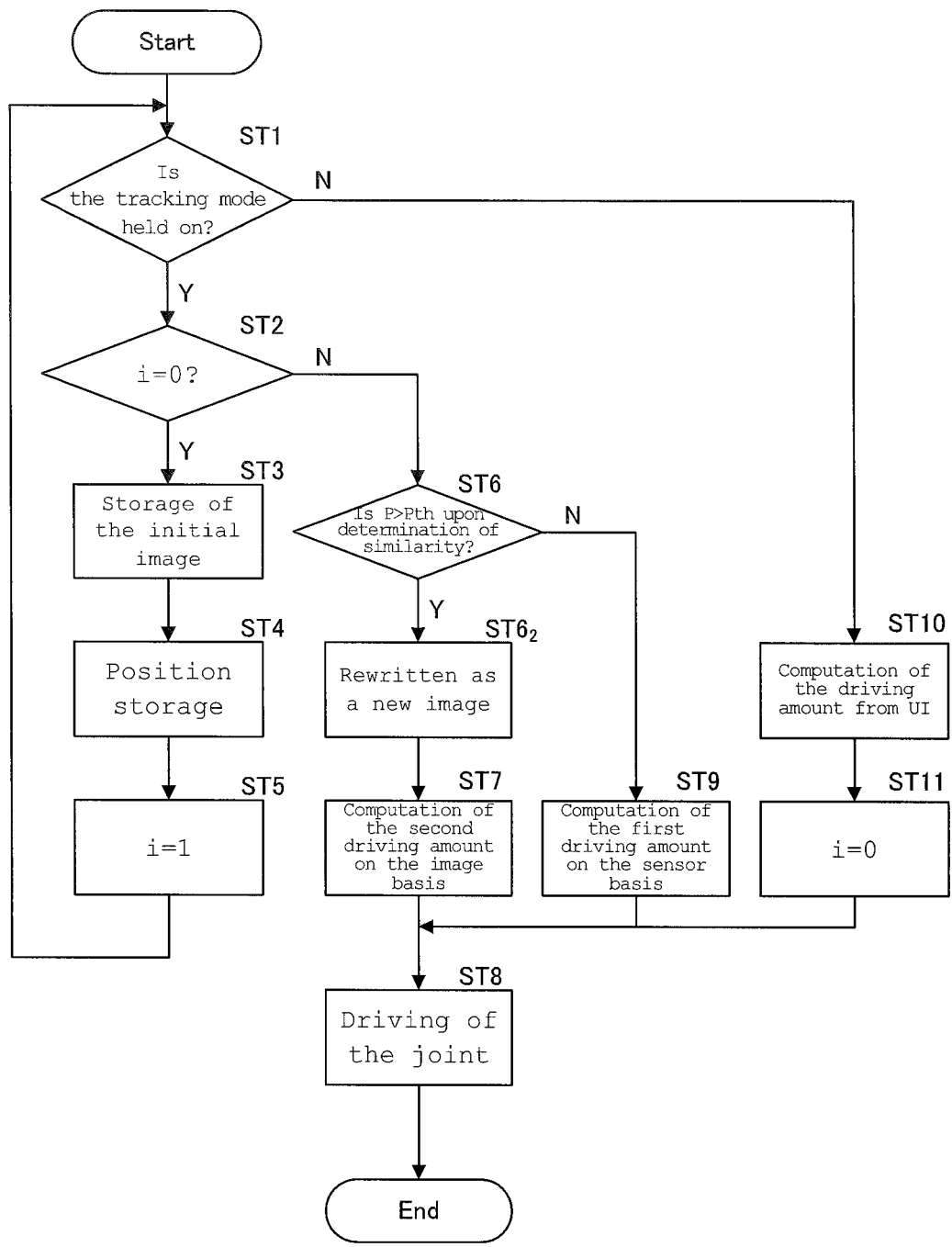
FIG. 12 is illustrative of one example of the control flowchart for the endoscope system according to the second embodiment.

FIG. 12 is representative of one example of the control flowchart for the endoscope system 10 according to the second embodiment.

Referring to control of the endoscope system 10 according to the second embodiment, after the degree of similarity P between the reference image $Pt_0$ of the imaging target Pt stored first at the counter i=0 and the current image $Pt_1$ of the imaging target Pt then at the counter i=1 is determined as being higher than the given value Pth in the similarity determination Step 6 in the control process according to the first embodiment, the processing goes to Step $6_2$ in which the reference image $Pt_0$ of the imaging target Pt stored first in the image storage unit 74 is erased and rewritten as the current image $Pt_1$ of the imaging target Pt that is then again stored ($ST6_2$).

For instance, presume now that the endoscope system 10 is placed in an initial state as shown in FIG. 6A with the counter set to the initial turn i=0 and the reference image $Pt_0$ of the imaging target of FIG. 6C is stored. At the next counter turn i=1, there is a new state appearing as shown in FIG. 8, and when the degree of similarity between it and the reference image $Pt_0$ of the imaging target of FIG. 6C is determined as being high, the current image $Pt_1$ of the imaging target Pt of FIG. 8B is overwritten and stored instead of the reference image $Pt_0$ of the imaging target Pt of FIG. 6C.

At the next turn, there is a state appearing as shown in FIGS. 10A and 10B, and when the degree of similarity between the current image $Pt_2$ of the imaging target Pt of FIG. 10B and the previous image $Pt_1$ of the imaging target Pt of FIG. 8B is determined as being high, the current image $Pt_2$ of the imaging target Pt shown in FIG. 10B is overwritten and stored instead of the previous image $Pt_1$ of the imaging target Pt shown in FIG. 8B.

That is, unless there is any abrupt change in the imaging target Pt, the field-of-view adjustment mechanism 1b is driven on the re-stored image basis. Note here that when there is an abrupt change due to the appearance of the treatment tool 3 such as forceps shown in FIGS. 11A and 11B, the field-of-view adjustment mechanism 1b may be driven on the sensor basis.

Thus, after the degree of similarity computed by the similarity computation unit 75 is determined as being higher than the predetermined value, the image $Pt_0$ of the imaging target Pt stored by the image storage unit 74 is erased, rewritten as the newly taken image $Pt_1$ of the imaging target Pt, and again stored. It is thus possible to improve on precision.

The endoscope control process includes a first image rewriting step in which when both the images compared in the image comparison step are determined as having a high degree of similarity, the previously stored image is rewritten as the current image taken by the imaging unit 1a. It is thus possible to improve on precision.

Figure 13:
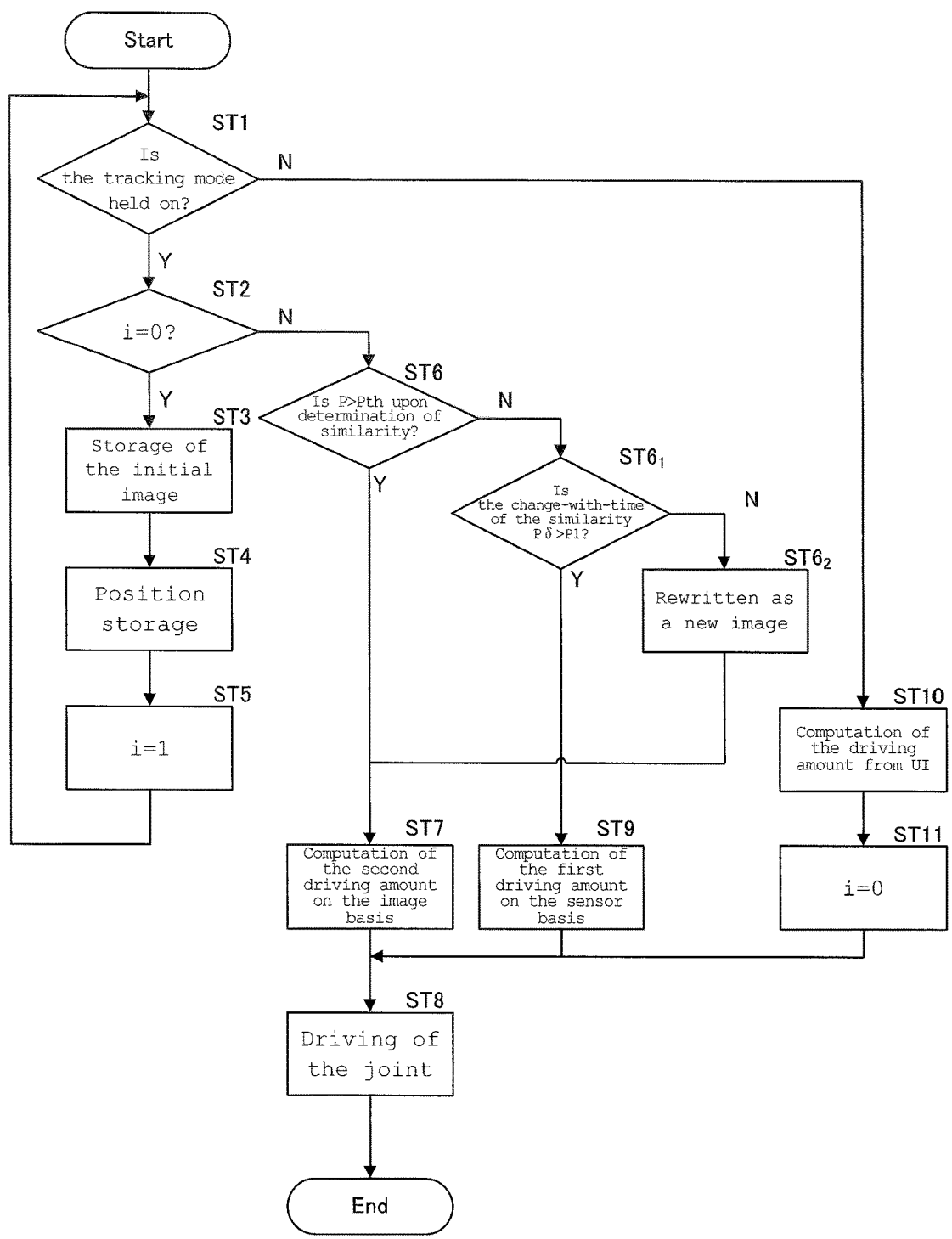
FIG. 13 is illustrative of one example of the control flowchart for the endoscope system according to the third embodiment.

FIG. 13 is representative of one example of the control flowchart for the endoscope system 10 according to the third embodiment.

Referring to another control of the endoscope system 10 according to the third embodiment, after the degree of similarity P between the reference image $Pt_0$ of the imaging target Pt stored first at the counter i=0 and the current image $Pt_1$ of the imaging target Pt at the counter i=1 is determined as being lower than the given value Pth in the similarity determination Step 6 in the control process according to the first embodiment, the processing goes to Step $6_1$ in which it is determined whether or not a change with time Pδ in the images' degree of similarity is greater than the predetermined value P1 ($ST6_1$).

In Step $6_1$, when the change with time Pδ in the images' degree of similarity is greater than the given value P1, the processing goes to Step 9 for sensor-based driving.

In Step $6_1$, when the change with time Pδ in the images' degree of similarity is less than the given value P1, the processing goes to Step $6_2$ in which the reference image $Pt_0$ of the imaging target is erased and rewritten by the image storage unit 74 as the image $Pt_1$ of the imaging target Pt after the elapse of a given time, and again stored ($ST6_2$), after which the processing goes to Step 7.

That is, when there is less change with time even upon abrupt changes in the imaging target Pt, a new image $Pt_1$ of the imaging target Pt after the elapse of a given time is again stored, and the field-of-view adjustment mechanism 1*b* is driven according to the image based second driving amount. For instance, when, even with a part of the affected site bleeding, the change in the image $Pt_1$ of the imaging target Pt remains less and stable after the elapse of a given time after bleeding, it is preferable that the image $Pt_1$ of the imaging target after the elapse of a given time after bleeding is again stored as a new reference image.

When the change with time of the degree of similarity is lower than the predetermined value after the degree of similarity computed by the similarity computation unit 75 is determined as being lower than the predetermined value, the image $Pt_0$ of the imaging target Pt stored in the image storage unit 74 may be erased, and rewritten and again stored as the new image $Pt_1$ of the imaging target Pt. It is thus possible to improve on precision.

Referring to the endoscope control process, when the degree of similarity between both the images is determined as being low in the image comparison step and the amount of change with time in the degree of similarity is greater than the given value, the driving amount is computed in the first driving-amount computation step. It is thus possible to improve on precision.

The endoscope control process described herein further includes the second image rewriting step in which, when the degree of similarity between both the images compared in the image comparison step is determined as being low and the amount of change with time in the degree of similarity is low, the recorded image is rewritten as a current image taken by the imaging unit 1*a*. It is thus possible to improve on precision.

Figure 14:
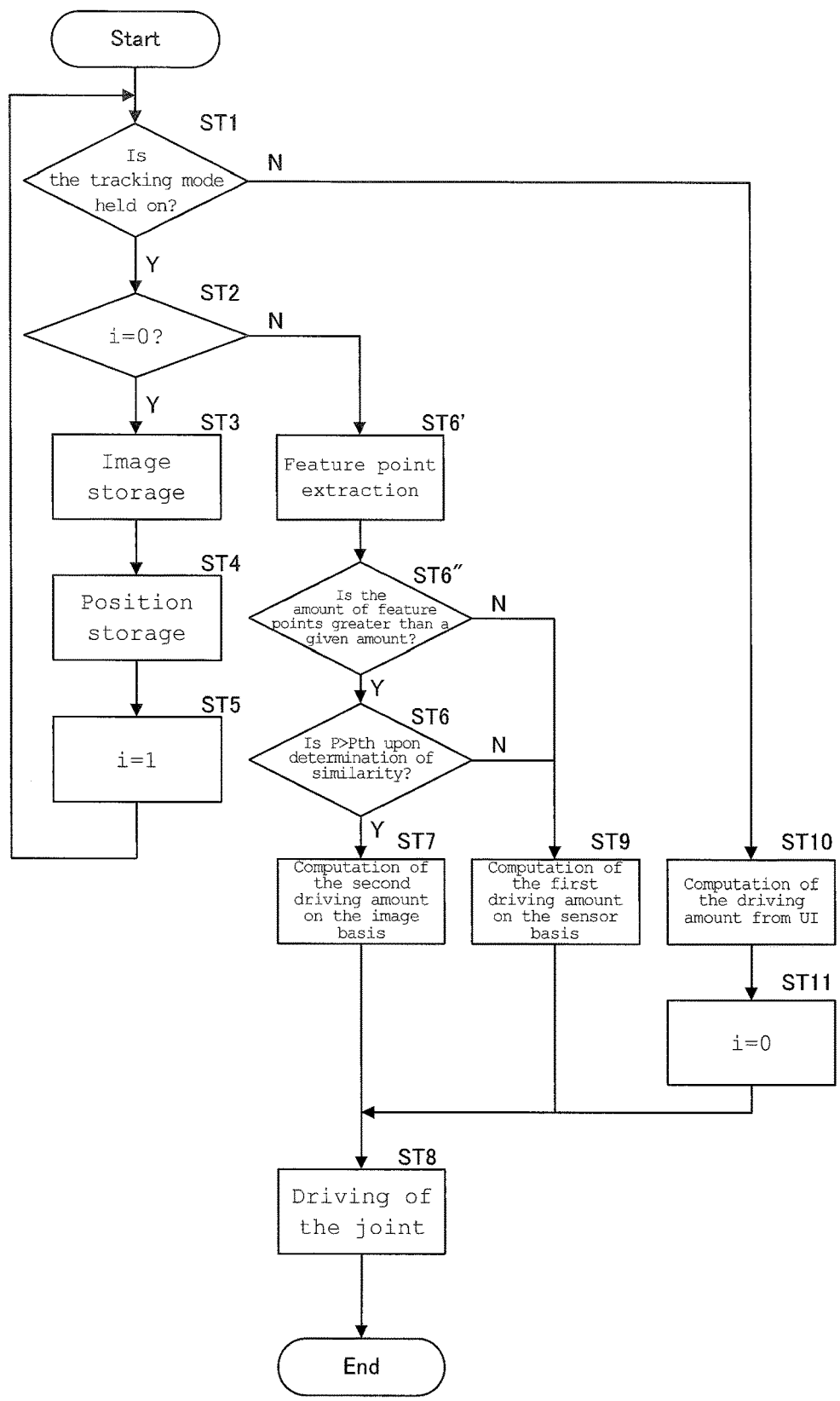
FIG. 14 is illustrative of one example of the control flowchart for the endoscope system according to the fourth embodiment.
Figure 15B:
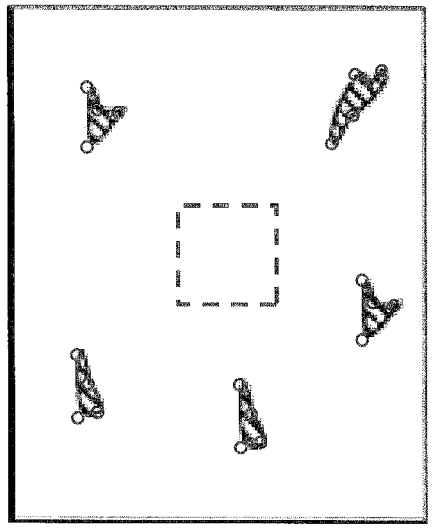
FIGS. 15A and 15B are illustrative of feature points in an image taken by the endoscope system according to the fourth embodiment.
Figure 15A:
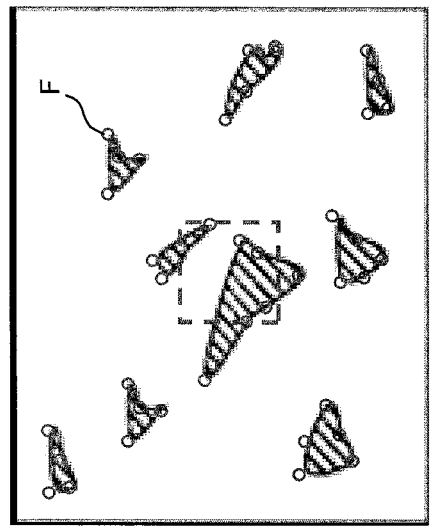

FIG. 14 is representative of a control flowchart for the endoscope system 10 according to the fourth embodiment. FIGS. 15A and 15B are illustrative of feature points in images taken by the endoscope system 10 according to the fourth embodiment: FIG. 15A is illustrative of more feature points in the image, and FIG. 15B is illustrative of fewer feature points F in the image.

The endoscope system 10 according to the fourth embodiment includes a feature point extraction unit for extracting feature points in an image and a feature point computation unit for determining whether or not the amount of extracted feature points is greater than a predetermined amount. In control of the endoscope system 10 according to the fourth embodiment, feature points F in the image are extracted in Step 6' prior to the similarity determination step 6 in the control according to the first embodiment (ST6'). For instance, portions distinguishable from the background, and their points of flexion, etc. may be used as the feature points F in the image, as shown in FIG. 15.

Then, the processing goes to Step 6" in which it is determined whether or not the amount of feature points F in the image is greater than a predetermined amount (ST6"). In an area including a fewer feature points F such as a nearly central area shown typically in FIG. 15B, any unerring degree of similarity cannot be obtained through comparison.

For this reason, in Step 6", when the amount of feature points F in the image is less than the predetermined amount, the processing goes to Step 9 driven on the sensor basis.

In Step 6", when the amount of feature points F in the image is greater than the predetermined amount, the processing goes to Step 6 in which control is implemented as in Embodiment 1.

It is here to be noted that the extraction of feature points F and the determination of the amount of feature points F implemented in Steps 6' and 6" may be carried out at any desired point in time prior to the determination of the degree of similarity in Step 6.

Thus, the endoscope system described herein includes the feature point extraction unit for extracting feature points in the image $Pt_0$ of the imaging target Pt stored in the image storage unit 74 or feature points in the new current image $Pt_1$ of the imaging target Pt, and when the amount of feature points extracted by the feature point extraction unit is less than the predetermined amount, the driver unit 8 is driven according to the first driving amount. Thus, the endoscope system here is well compatible with even when the amount of feature points is too small for similarity comparison. Note here that the size of an area for which the amount of feature points is determined may be variable.

The endoscope control process described herein further includes the feature point extraction unit for extracting feature points in the current image taken by the imaging unit 1*a*, and when the amount of feature points is less than the given amount in the feature point extraction step, the driving amount is computed in the first driving-amount computation step whereas, when the amount of feature points in the feature point extraction unit is more than the given amount, both the images are compared in the image comparison step. Thus, the endoscope control process here is well compatible with even when the amount of feature points is too small for similarity comparison.

Figure 16:
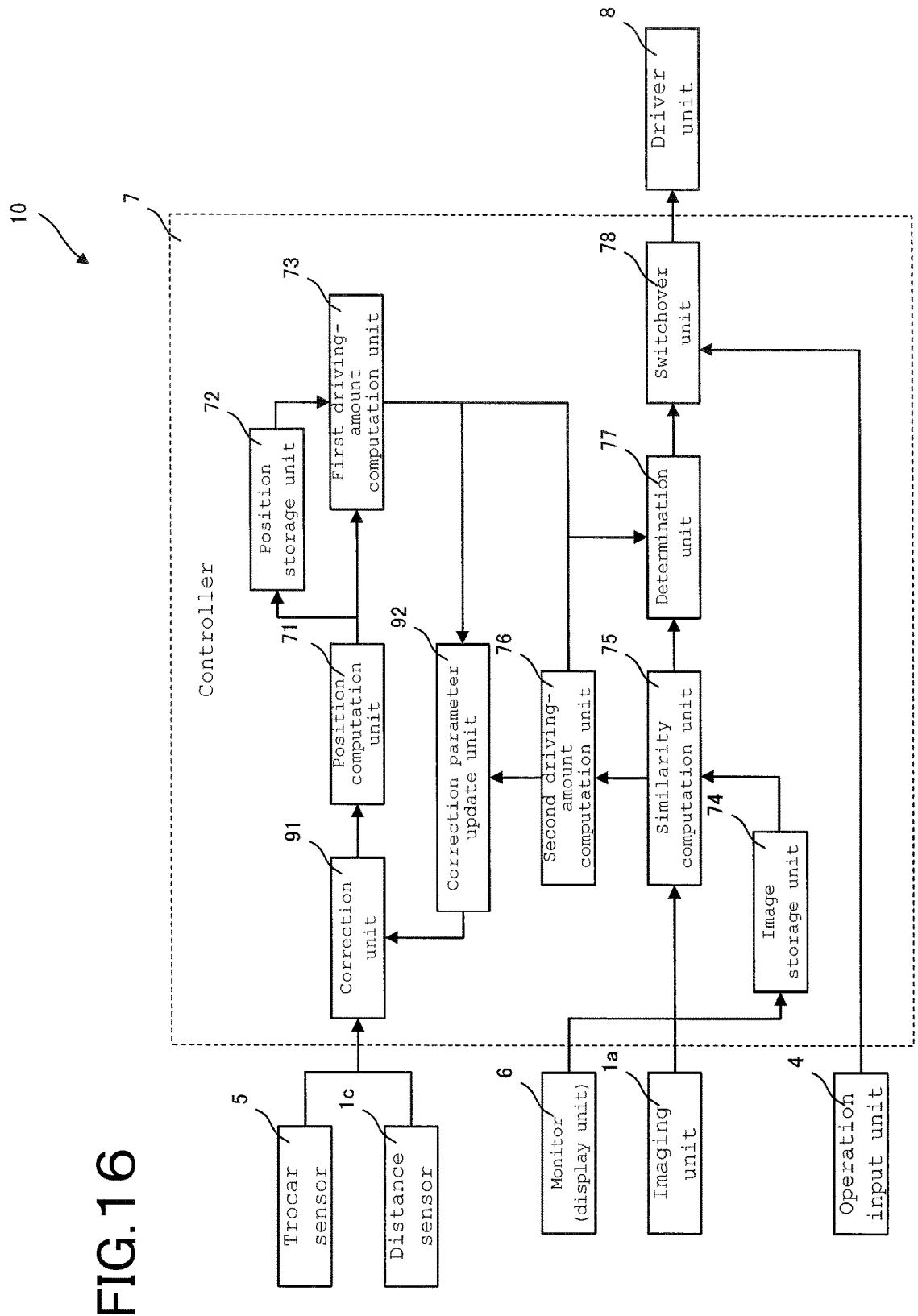
FIG. 16 is illustrative of one example of the system diagram for the endoscope system according to the fifth embodiment.

FIG. 16 is illustrative of one example of the system diagram for the endoscope system 10 according to the fifth embodiment.

The endoscope system 10 according to the fifth embodiment includes a correction unit 91 for correcting input signals from the trocar sensor 5 and distance sensor 1*c*, and a correction parameter update unit 92 for comparing values computed by the first and second driving-amount computation units 73 and 76 to acquire detection errors for each sensor thereby updating the correction parameter for the correction unit 91.

The endoscope system 10 described herein may be controlled on the image basis or the sensor basis. A sensor may possibly have an initial error on production or an error with time. In the endoscope system 10 according to the fifth embodiment, therefore, the value computed by the first driving-amount computation unit 73 for computing the driving amount on the sensor basis is compared with the value computed by the second driving-amount computation unit 76 for computing the driving amount on the image basis to find the correction parameter by the correction parameter update unit 92, on the basis of which input signals to the respective sensors are corrected at the correction unit 91. Thus, the input signals from the trocar sensor 5 and distance sensor 1*c* are corrected and then entered in the position computation unit 71.

By correcting the input signals to the respective sensor 5 and 1*c* by the correction unit 91, it is thus possible to improve the precision of computation of the driving amount on the sensor basis. Note here that correction by the correction unit 91 and updating of the correction parameter by the correction parameter update unit 92 may be implemented at any desired point in time. For instance, the correction parameter may have been updated prior to getting control started, and correction may be carried out by the correction unit 91 at the time of computing the driving amount on the sensor basis or, alternatively, the correction parameter may be updated by the correction parameter update unit 92 at the time of computation of the driving amount on the sensor basis for correction by the correction unit 91.

Figure 17A:
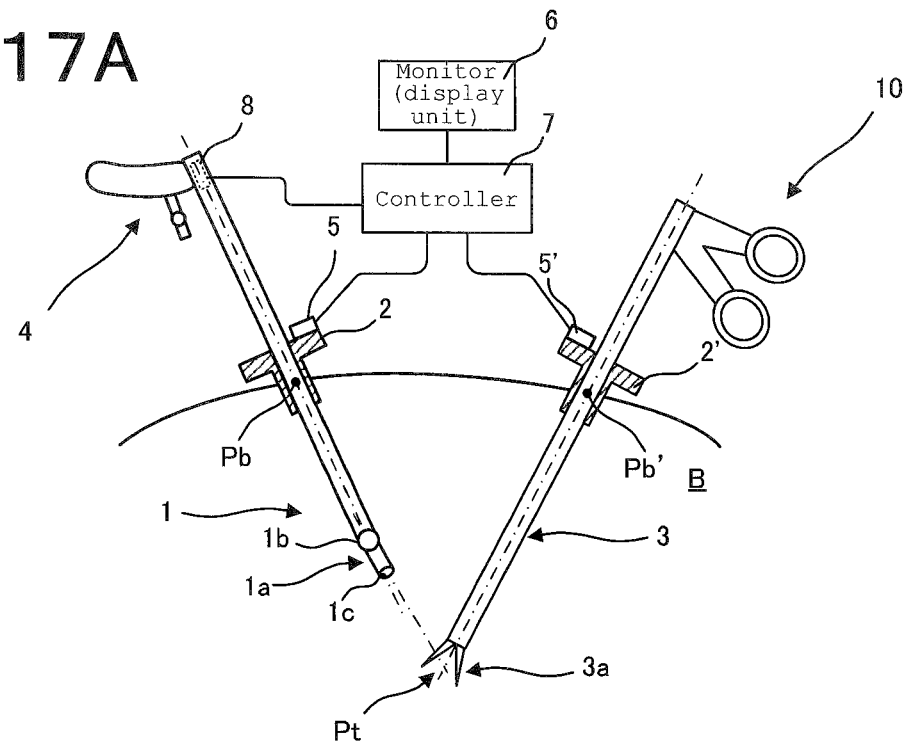
FIGS. 17A, 17B and 17C are illustrative of a state in which an image is stored by the endoscope system according to the sixth embodiment.
Figure 17B:
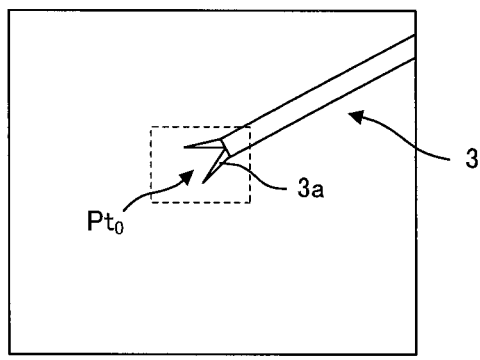
Figure 17C:
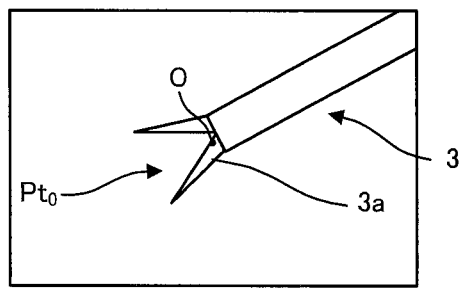

FIGS. 17A, 17B and 17C are illustrative of a state of storing images in the endoscope system 10 according to the sixth embodiment and the then display unit 6: FIG. 17A is illustrative of storing images in the endoscope system 10 according to the sixth embodiment, FIG. 17B is illustrative of the then display unit 6, and FIG. 17C is representative of the reference image $Pt_0$.

In the endoscope system 10 according to the sixth embodiment, the distal end portion 3a of the treatment tool 3 is used as the imaging target Pt.

As depicted in FIG. 17A, the second trocar 2' through which the treatment tool 3 is inserted is rotatable about a fulcrum Pb', and the second trocar sensor 5' working here as a second position sensor is capable of detecting at least the tilt angle of the second trocar 2' and the amount of insertion of the treatment tool 3 through the second trocar 2' as is the case with the trocar sensor 5.

The endoscope system 10 according to the sixth embodiment is basically controlled pursuant to a control flowchart similar to that of FIG. 5.

Referring to the image storage step defined by Step 3 shown in FIG. 5, the reference image $Pt_0$ of the imaging target Pt being currently taken by the imaging unit 1a is stored in the image storage unit 74 shown in FIG. 4. Specifically, the imaging unit 1a of the endoscope 1 is operated by the surgeon such that an image of the distal end portion 3a of the treatment tool 3 that defines the imaging target Pt appears as shown in FIG. 17B. In this state, as there is an instruction given by the surgeon to store the reference image $Pt_0$ of the imaging target Pt, it causes the image of the distal end portion 3a of the treatment tool 3 that defines the imaging target Pt to be stored as the reference $Pt_0$, as shown in FIG. 17C.

Referring to the position storage of Step 4, the position of the treatment tool 3 is also stored in addition to the position of the endoscope 1. That is, in Step 4, the positions of the endoscope's distal end and the distal end portion 3a of the treatment tool 3 that defines the imaging target Pt are computed by the position computation unit 71 shown in FIG. 4 on the basis of information entered from the trocar sensor 5 and distance sensor 1c of the endoscope 1 and information entered from the second trocar sensor 5' of the treatment tool 3. Then, those positions are stored in the position storage unit 72.

After that, the degree of similarity P is computed in Step 6 to determine whether the joint is to be driven on the sensor basis or the image basis.

Figure 18A:
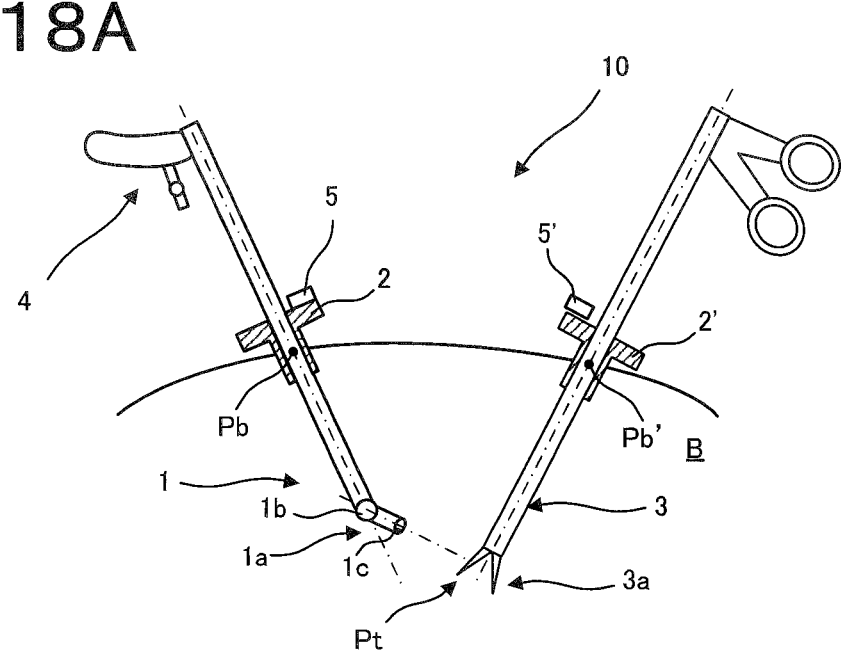
FIGS. 18A and 18B are illustrative of a state having a high degree of similarity upon movement of the treatment tool 3 in the endoscope system according to the sixth embodiment.
Figure 18B:
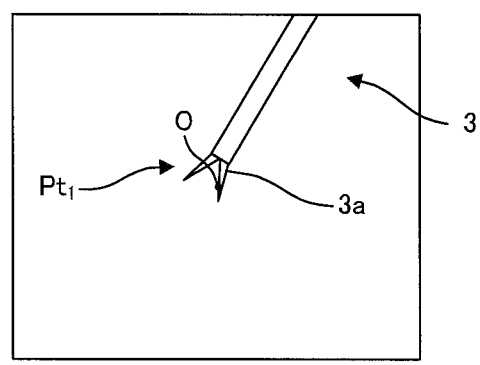

FIG. 18 is illustrative of a state where there is a high degree of similarity upon movement of the treatment tool 3 in the endoscope system 10 according to the sixth embodiment and the then display unit 6: FIG. 18A is illustrative of a state where there is a high degree of similarity upon movement of the treatment tool 3 in the endoscope system 10 according to the sixth embodiment, and FIG. 18B is illustrative of the then display unit 6.

When the degree of similarity P is greater than the given value Pth upon movement of the treatment tool 3 by the surgeon from the storage position shown in FIG. 17A to the first position shown in FIG. 18A, the processing for the endoscope system 10 goes to Step 7 shown in FIG. 5 in which the image-based second driving amount is computed. Then, the field-of-view adjustment mechanism 1b of the endoscope 1 is driven on the basis of the second driving amount to vary the orientation of the imaging unit 1a so that the current image $Pt_1$ of the imaging target Pt is nearly centered in such a way as to include at least the center O of the display screen, as shown in FIG. 18B. In other words, the endoscope 1 comes to follow the movement of the treatment tool 3.

Figure 19A:
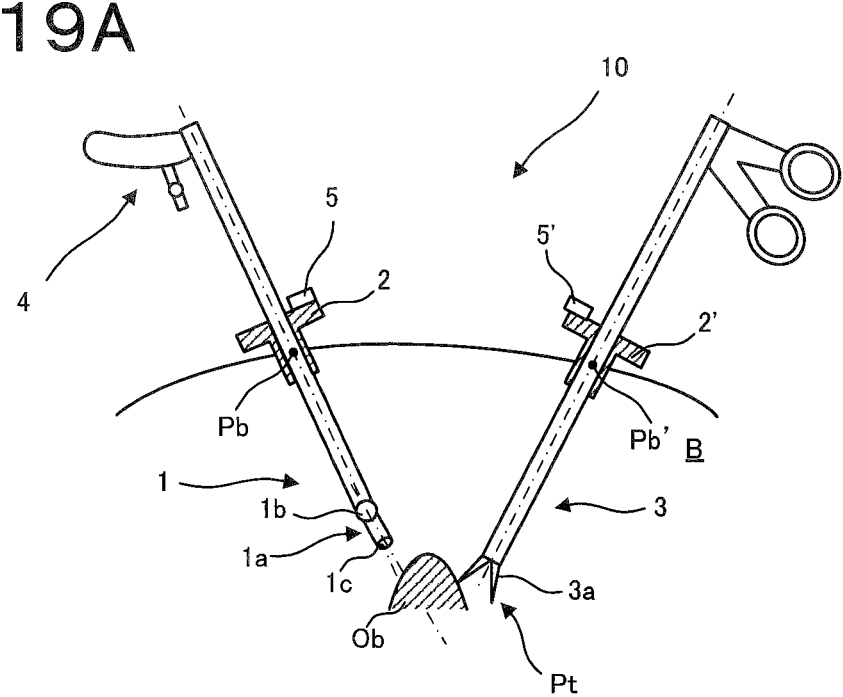
FIGS. 19A and 19B are illustrative of a state having a low degree of similarity upon movement of the treatment tool 3 in the endoscope system according to the sixth embodiment.
Figure 19B:
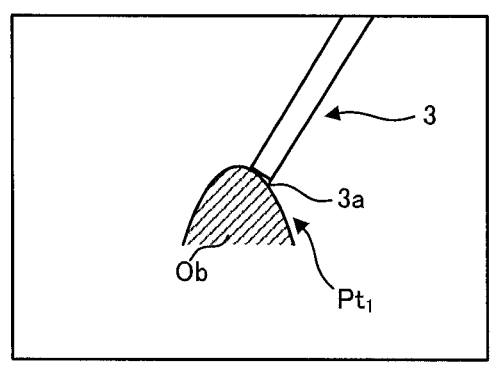

FIGS. 19A and 19B are illustrative of a state where there is a low degree of similarity upon movement of the treatment tool 3 in the endoscope system 10 according to the sixth embodiment and the then display unit 6: FIG. 19A is illustrative of a state where there is a low degree of similarity upon movement of the treatment tool 3 in the endoscope system 10 according to the sixth embodiment, and FIG. 19B is illustrative of the then display unit 6.

When the treatment tool 3 is moved by the surgeon from the storage position shown in FIG. 17A to the second position shown in FIG. 19A, the degree of similarity P is less than the given value Pth if there is an obstacle Ob such as body tissue present between the imaging unit 1a and the imaging target Pt. In this case, the processing for the endoscope system 10 goes to Step 9 shown in FIG. 5 in which the sensor-based first driving amount is computed from measurements obtained from the trocar sensor 5 and distance sensor 1c and measurements obtained from the second trocar sensor 5'. Then, the endoscope 1 enables the field-of-view adjustment mechanism 1b to be driven to vary the orientation of the imaging unit 1a so that the current image $Pt_1$ of the imaging target Pt is centered as shown in FIG. 19B. In other words, the endoscope 1 comes to follow the movement of the treatment tool 3.

In the endoscope system 10 according to the sixth embodiment described herein, the distal end portion 3a of the treatment tool 3 is used as the imaging target Pt. It is thus possible to improve on operability because the endoscope 1 is driven following the movement of the treatment tool 3 so that the treatment tool 3 appears always within the display screen.

Figure 20:
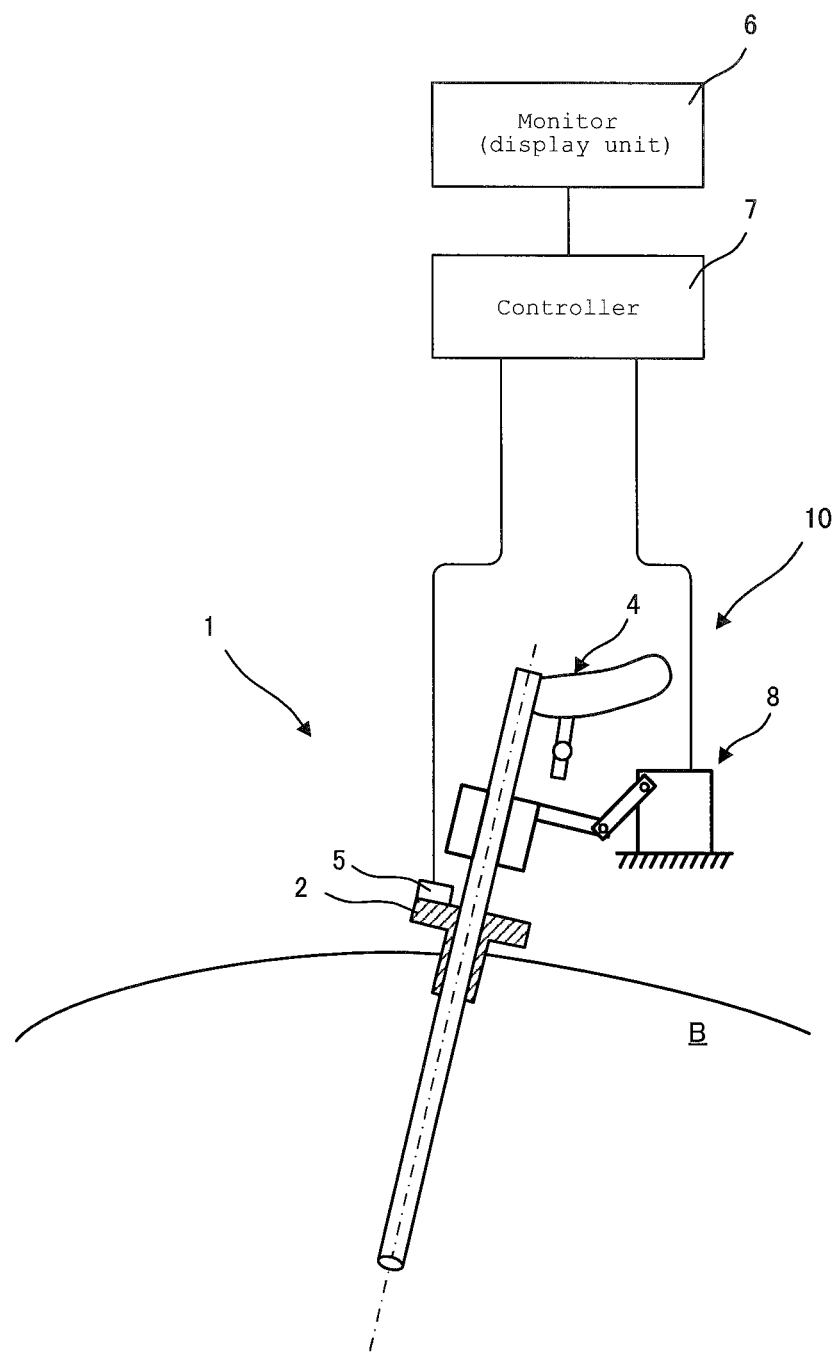
FIG. 20 is a schematic view of one example of the endoscope system 10 according to a further embodiment.

FIG. 20 is a schematic view of one example of the endoscope system 10 according to another embodiment.

In the example shown in FIG. 20, the endoscope 1 includes the driver unit 8 that is located outside the body cavity. The driver unit 8 includes an actuator by which the endoscope 1 can be driven in a advanceable/retractable movement direction, a tilting direction and a rotating direction about the axis.

The endoscope system 10 according to the embodiments described herein may also be embodied in other possible forms.

For instance, multiple positions may be stored in the position storage unit 72 with a selection unit for selecting the position to be followed out of the stored multiple positions. In this case, names may be given to the stored multiple positions to display them on the display unit 6. Alternatively, in the vicinity of the direction indication mark, the name of a position corresponding to that direction indication mark may be displayed. While the hard endoscope 1 has been taken as an example in the present disclosure, it is to be understood that a flexible or soft endoscope may also be used.

In the embodiments described herein, while parameters such as positions and driving amounts are figured out by giving input values to a variety of preset mathematical formulae, it is to be appreciated that the desired numerical values may be derived with reference to a preset lookup table (correspondence table) with the input values as key or, alternatively, mathematical formulae may be combined with the table.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope. In other words, illustrative embodiments are described without excluding generality from the claimed inventions and imposing any limitation thereon.

REFERENCE SIGNS LIST

1: Endoscope
1a: Imaging unit
1b: Field-of-view adjustment mechanism
1c: Distance sensor (distance measurement unit)
2: Trocar
3: Treatment tool
4: Operation input unit
5: Trocar sensor (endoscopic position sensor)
7: Control unit (controller)
71: Position computation unit
72: Position storage unit
73: First driving-amount computation unit
74: Image storage unit
75: Similarity computation unit (comparison unit)
76: Second driving-amount computation unit
77: Determination unit
78: Switchover unit
8: Driver unit
91: Correction unit
92: Correction parameter update unit
10: Endoscope system

The invention claimed is:

1. An endoscope system comprising:
an endoscope comprising:
an image sensor configured to take an image of an imaging target;
a field-of-view adjustment mechanism configured to vary an orientation of the image sensor; and
a driver configured to drive the field-of-view adjustment mechanism to vary the orientation of the image sensor;
an endoscopic position sensor configured to detect a position of the endoscope in a body cavity;
a distance sensor configured to measure a distance from a distal end of the endoscope to the imaging target; and
a processor comprising hardware, wherein the processor is configured to:
compute positions of the distal end of the endoscope and the imaging target on the basis of the position of the endoscope in the body cavity detected by the endoscopic position sensor and the distance from the distal end of the endoscope to the imaging target measured by the distance sensor;
control one or more storages to store a position of the imaging target computed;
compute a first driving amount by which the field-of-view adjustment mechanism is driven by the driver to vary the orientation of the image sensor based on the position of the imaging target computed stored in the one or more storages and the position of the distal end of the endoscope computed;
control the one or more storages to store the image of the imaging target taken by the image sensor;
perform a comparison of the image of the imaging target stored in the one or more storages with a newly taken image of the imaging target to determine a degree of similarity between the image of the imaging target stored in the one or more storages and the newly taken image of the imaging target;
compute a second driving amount by which the field-of-view adjustment mechanism is driven by the driver to vary the orientation of the image sensor based on a result of comparison; and
select one of the first driving amount and the second driving amount by which the field-of-view adjustment mechanism is driven by the driver to vary the orientation of the image sensor based on the degree of similarity determined,
wherein the processor is configured to:
in response to determining that the degree of similarity is lower than a first predetermined value, determine whether a change with time in the degree of similarity is less than a second predetermined value; and
in response to determining that the change with time in the degree of similarity is less than the second predetermined value, control the one or more storages to store the newly taken image of the imaging target as the image of the imaging target,
wherein the processor is configured to:
correct a position of the endoscope in the body cavity detected by the endoscopic position sensor;
compare the first driving amount and the second driving amount to acquire a detection error for the endoscopic position sensor; and
update a correction parameter by which the position of the endoscope in the body cavity detected by the endoscopic position sensor is corrected,
wherein when the degree of similarity is lower than the first predetermined value, the processor is configured to drive the driver according to the first driving amount, and
wherein when the degree of similarity is higher than the first predetermined value, the processor is configured to drive the driver according to the second driving amount.

2. The endoscope system according to claim 1, wherein the processor is configured to, in response to determining that the degree of similarity is higher than the first predetermined value, control the one or more storages to store the newly taken image of the imaging target as the image of the imaging target.

3. The endoscope system according to claim 1, wherein the processor is configured to:
extract feature points in the image of the imaging target or the newly taken image of the imaging target;
determine whether an amount of feature points extracted is less than a predetermined amount; and
in response to determining that the amount of feature points extracted is less than the predetermined amount, control the driver to drive the field-of-view adjustment mechanism to vary the orientation of the image sensor by the first driving amount.

4. The endoscope system according to claim 1, further comprising:
an endoscopic trocar through which the endoscope is inserted into the body cavity, wherein the endoscopic position sensor comprises an endoscopic trocar sensor attached to the endoscopic trocar, wherein the endoscopic trocar sensor is configured to measure a distal end position of the image sensor in the body cavity.

5. The endoscopic system according to claim 1,
wherein the processor is configured to control a display to display which of the first driving amount and the second driving amount is selected.

6. The endoscope system according to claim 1, further comprising:
   a treatment tool configured to apply treatments within the body cavity;
   a treatment tool trocar through which the treatment tool is inserted; and
   a treatment tool position sensor attached to the treatment tool trocar, wherein the treatment tool position sensor is configured to measure a distal end position of the treatment tool,
   wherein the processor is configured to:
      compute the first driving amount based on the position of the imaging target computed stored in the one or more storages, the position of the distal end of the endoscope computed and the distal end position of the treatment tool measured; and
      compute the second driving amount based on the result of the comparison and the distal end position of the treatment tool measured.

7. A method of controlling an endoscope system comprising:
   an endoscope comprising:
      an image sensor configured to take an image of an imaging target;
      a field-of-view adjustment mechanism configured to vary an orientation of the image sensor; and
      a driver configured to drive the field-of-view adjustment mechanism to vary the orientation of the image sensor;
   an endoscopic position sensor configured to detect a position of the endoscope in a body cavity; and
   a distance sensor configured to measure a distance from a distal end of the endoscope to the imaging target,
   wherein the method comprises:
      computing positions of the distal end of the endoscope and the imaging target on the basis of the position of the endoscope in the body cavity detected by the endoscopic position sensor and the distance from the distal end of the endoscope to the imaging target measured by the distance sensor;
      controlling one or more storages to store a position of the imaging target computed;
      computing a first driving amount by which the field-of-view adjustment mechanism is driven by the driver to vary the orientation of the image sensor based on the position of the imaging target computed stored in the one or more storages and the position of the distal end of the endoscope computed;
      controlling the one or more storages to store the image of the imaging target taken by the image sensor;
      performing a comparison of the image of the imaging target stored in the one or more storages with a newly taken image of the imaging target to determine a degree of similarity between the image of the imaging target stored in the one or more storages and the newly taken image of the imaging target;
      computing a second driving amount by which the field-of-view adjustment mechanism is driven by the driver to vary the orientation of the image sensor based on a result of comparison; and
      selecting one of the first driving amount and the second driving amount by which the field-of-view adjustment mechanism is driven by the driver to vary the orientation of the image sensor based on the degree of similarity determined,
   wherein the method comprises:
      in response to determining that the degree of similarity is lower than a first predetermined value, determining whether a change with time in the degree of similarity is less than a second predetermined value; and
      in response to determining that the change with time in the degree of similarity is less than the second predetermined value, controlling the one or more storages to store the newly taken image of the imaging target as the image of the imaging target,
   wherein the method comprises:
      correcting a position of the endoscope in the body cavity detected by the endoscopic position sensor;
      comparing the first driving amount and the second driving amount to acquire a detection error for the endoscopic position sensor; and
      updating a correction parameter by which the position of the endoscope in the body cavity detected by the endoscopic position sensor is corrected, and
   wherein the method comprises:
      when the degree of similarity is lower than the first predetermined value, driving the driver according to the first driving amount; and
      when the degree of similarity is higher than the first predetermined value, driving the driver according to the second driving amount.

8. The method according to claim 7, comprising:
in response to determining that the degree of similarity is higher than the first predetermined value, controlling the one or more storages to store the newly taken image of the imaging target as the image of the imaging target.

9. The method according to claim 7, comprising:
extracting feature points in the image of the imaging target or the newly taken image of the imaging target;
determining whether an amount of feature points extracted is less than a predetermined amount; and
in response to determining that the amount of feature points extracted is less than the predetermined amount, controlling the driver to drive the field-of-view adjustment mechanism to vary the orientation of the image sensor by the first driving amount.

10. The method according to claim 7, comprising:
controlling a display to display which of the first driving amount and the second driving amount is selected.

11. The method according to claim 7,
wherein the endoscope system comprises:
   a treatment tool configured to apply treatments within the body cavity;
   a treatment tool trocar through which the treatment tool is inserted; and
   a treatment tool position sensor attached to the treatment tool trocar, wherein the treatment tool position sensor is configured to measure a distal end position of the treatment tool,
wherein the method comprises:
   computing the first driving amount based on the position of the imaging target computed stored in the one or more storages, the position of the distal end of the endoscope computed and the distal end position of the treatment tool measured; and computing the second driving amount based on the result of the comparison and the distal end position of the treatment tool measured.

12. An endoscope system comprising:

an endoscope comprising:
   an image sensor configured to take an image of an imaging target;
   a field-of-view adjustment mechanism configured to vary an orientation of the image sensor; and
   a driver configured to drive the field-of-view adjustment mechanism to vary the orientation of the image sensor;
an endoscopic position sensor configured to detect a position of the endoscope in a body cavity;
a distance sensor configured to measure a distance from a distal end of the endoscope to the imaging target; and
a processor comprising hardware, wherein the processor is configured to:
   compute positions of the distal end of the endoscope and the imaging target on the basis of the position of the endoscope in the body cavity detected by the endoscopic position sensor and the distance from the distal end of the endoscope to the imaging target measured by the distance sensor;
   control one or more storages to store a position of the imaging target computed;
   compute a first driving amount by which the field-of-view adjustment mechanism is driven by the driver to vary the orientation of the image sensor based on the position of the imaging target computed stored in the one or more storages and the position of the distal end of the endoscope computed;
   control the one or more storages to store the image of the imaging target taken by the image sensor;
   perform a comparison of the image of the imaging target stored in the one or more storages with a newly taken image of the imaging target to determine a degree of similarity between the image of the imaging target stored in the one or more storages and the newly taken image of the imaging target;
   compute a second driving amount by which the field-of-view adjustment mechanism is driven by the driver to vary the orientation of the image sensor based on a result of comparison; and
   select one of the first driving amount and the second driving amount by which the field-of-view adjustment mechanism is driven by the driver to vary the orientation of the image sensor based on the degree of similarity determined,
wherein the processor is configured to:
   in response to determining the degree of similarity based on a first predetermined value, determine whether a change with time in the degree of similarity is less than a second predetermined value; and
   in response to determining that the change with time in the degree of similarity is less than the second predetermined value, control the one or more storages to store the newly taken image of the imaging target as the image of the imaging target,
wherein the processor is configured to:
   correct a position of the endoscope in the body cavity detected by the endoscopic position sensor;
   compare the first driving amount and the second driving amount to acquire a detection error for the endoscopic position sensor; and
   update a correction parameter by which the position of the endoscope in the body cavity detected by the endoscopic position sensor is corrected,
wherein when the degree of similarity is lower than the first predetermined value, the processor is configured to drive the driver according to the first driving amount, and
wherein when the degree of similarity is higher than the first predetermined value, the processor is configured to drive the driver according to the second driving amount.

* * * * *